(12) United States Patent
Loh et al.

(10) Patent No.: US 11,583,612 B2
(45) Date of Patent: Feb. 21, 2023

(54) MATERIAL SUITABLE FOR USE AS A VITREOUS SUBSTITUTE AND RELATED METHODS

(71) Applicants: Agency for Science, Technology and Research, Singapore (SG); National University Hospital (Singapore) Pte Ltd, Singapore (SG); National University of Singapore, Singapore (SG); Singapore Health Services Pte Ltd, Singapore (SG)

(72) Inventors: Xian Jun Loh, Singapore (SG); Xinyi Su, Singapore (SG); Zengping Liu, Singapore (SG); Gopal Lingam, Singapore (SG); Veluchamy Amutha Barathi, Singapore (SG); Walter Hunziker, Singapore (SG)

(73) Assignees: Agency for Science, Technology and Research, Singapore (SG); National University Hospital (Singapore) Pte Ltd, Singapore (SG); National University of Singapore, Singapore (SG); Singapore Health Services Pte Ltd, Singapore (SG)

( * ) Notice: Subject to any disclaimer, the term of this patent is extended or adjusted under 35 U.S.C. 154(b) by 294 days.

(21) Appl. No.: 16/804,586

(22) Filed: Feb. 28, 2020

(65) Prior Publication Data
US 2020/0276357 A1  Sep. 3, 2020

(30) Foreign Application Priority Data
Feb. 28, 2019  (SG) .......................... 10201901837Q

(51) Int. Cl.
*A61L 27/18* (2006.01)
*C08G 81/00* (2006.01)

(52) U.S. Cl.
CPC .............. *A61L 27/18* (2013.01); *C08G 81/00* (2013.01); *A61L 2430/16* (2013.01)

(58) Field of Classification Search
None
See application file for complete search history.

(56) References Cited

U.S. PATENT DOCUMENTS

2016/0058698 A1\* 3/2016 Mayadunne .......... A61K 9/0024
                                                     514/262.1
2016/0325009 A1\* 11/2016 Cohn .................. A61L 24/0042
(Continued)

OTHER PUBLICATIONS

European Application No. EP 20159934.7 received a Search Report dated Jul. 8, 2020, 8 pages.
(Continued)

*Primary Examiner* — Peter A Salamon
(74) *Attorney, Agent, or Firm* — Kilpatrick Townsend & Stockton LLP

(57) ABSTRACT

There is provided a material comprising a multi-block thermogelling polymer, said multi-block thermogelling polymer comprising a hydrophilic polymer block; a thermosensitive polymer block; and a hydrophobic polymer block, wherein the hydrophilic polymer block, the thermosensitive polymer block and the hydrophobic polymer block are chemically coupled together by at least one of urethane/carbamate, carbonate, ester linkages or combinations thereof, and wherein the material is suitable for use as a vitreous substitute. Also provided are a method of preparing said material and a synthetic vitreous humour or part thereof comprising said material.

22 Claims, 40 Drawing Sheets

(56) References Cited

U.S. PATENT DOCUMENTS

2018/0094099 A1* 4/2018 Johnson ............... C08G 61/02
2020/0276357 A1* 9/2020 Loh ...................... A61L 27/18

OTHER PUBLICATIONS

Chinese Patent Application No. 202010131156.9, Office Action dated May 24, 2022, 16 pages.

Loh XJ, et al., Sustained delivery of paclitaxel using thermogelling poly(PEG/PPG/PCL urethane)s for enhanced toxicity against cancer cells. J Biomed Mater Res A. 2012;100(10):2686-2694. doi:10.1002/jbm.a.34198.

Su X, et al., Recent Progress in Using Biomaterials as Vitreous Substitutes. Biomacromolecules. 2015;16(10):3093-3102. doi:10.1021/acs.biomac.5b01091.

\* cited by examiner

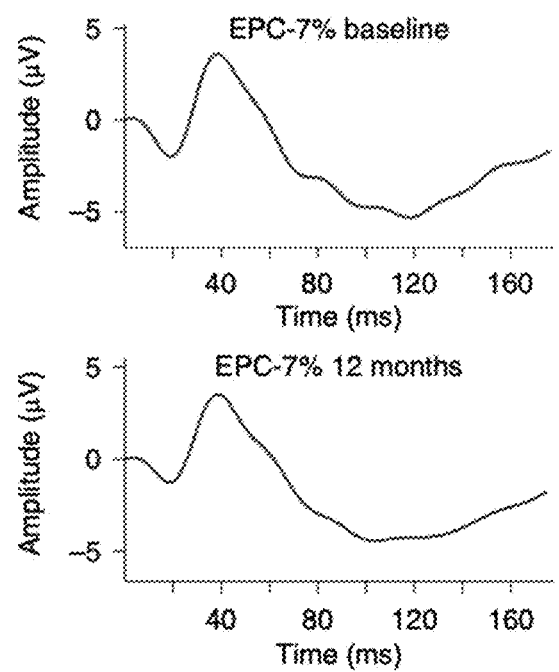
FIG. 22C
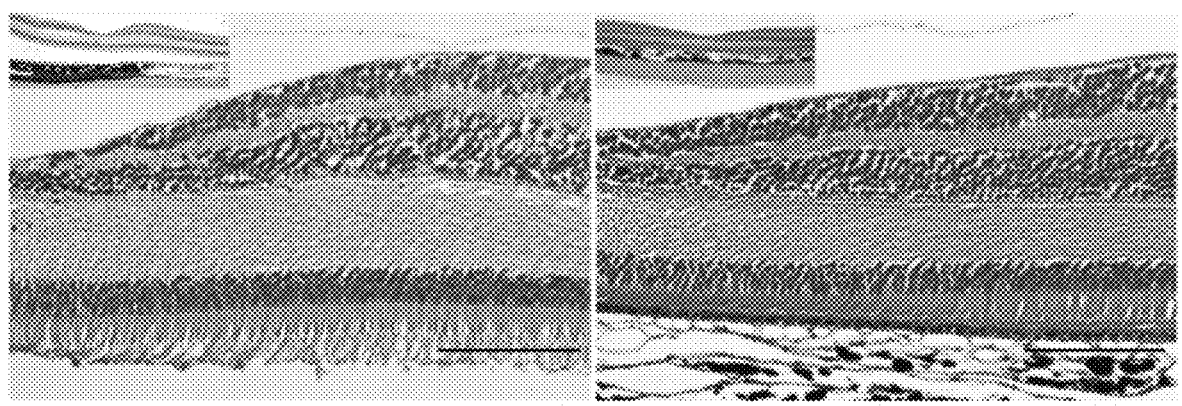
FIG. 22D                              FIG. 22E

MATERIAL SUITABLE FOR USE AS A VITREOUS SUBSTITUTE AND RELATED METHODS

CROSS-REFERENCE TO RELATED APPLICATION

This application claims priority to Singapore Patent Application No. 10201901837Q, filed Feb. 28, 2019, the disclosure of which is incorporated by reference herein in its entirety.

TECHNICAL FIELD

The present disclosure relates broadly to a material that is suitable for use as a vitreous humour substitute and related methods. The present disclosure also relates to a synthetic vitreous humour substitute.

BACKGROUND

The vitreous is a clear, gelatinous substance occupying the vitreous cavity. Composed of 98-99 wt % water, the vitreous is a natural polymeric hydrogel constituted primarily of collagen fibers and hyaluronic acid. In addition to the maintenance of normal orbit turgor to position the retina, the vitreous has important physiological functions in the circulation of metabolites and nutrients. Ageing and vitreous degeneration increase the liquefaction of the vitreous, which may result in increased vitreo-retinal traction and cause sight-threatening conditions such as retinal detachment.

Retinal detachment is the fifth leading cause of blindness in developing countries. During retinal detachment repair, vitrectomy surgery (whereby vitreous is removed from the eye) is performed to relieve vitreous traction. As the vitreous humor cannot regenerate de novo, the cavity must be filled with a substitute during and after surgery. Ideally, this substitute should closely resemble native vitreous in both structure and function. Post-surgery, it has to act as an endotamponade agent to facilitate re-adhesion of the detached neurosensory retina to the underlying retinal pigment epithelium. However, the search for a suitable vitreous substitute remains challenging. Indeed, current substitutes used have several limitations and are far from desirable. This is further elaborated below.

In current clinical practice, materials used include perfluoro-carbon liquids that are used as temporary intra-operative tamponade, and expansile gases and silicone oil that are used for medium and long-term tamponade, respectively. However, there are multiple disadvantages related to their usage, as summarised in Table 1. For example, gaseous substitutes need face-down positioning for several weeks post-surgery (due to buoyancy forces) and patients are unable to travel by air. Silicone oil substitutes require additional removal surgery with potential complications, including raised intra-ocular pressure, temporary loss of vision, cataract formation and long-term retinal toxicity.

TABLE 1

A summary of the limitations of current vitreous tamponades

| Available Vitreous Substitutes | Physical Status | Remarks Advantages | Disadvantages |
|---|---|---|---|
| Air | Gas | High surface tension | Short residence time (few days) |
| $SF_6/C_3F_8$ | Gas | High success rate (~90% for retinopexy) Suitable for short-term vitreous substitutes | Sudden increase in intraocular pressure, cataract formation Prolonged, face-down positioning post-operatively for up to 4 weeks Unable to travel by air/diving Less effective for inferior retinal detachment (RD) |
| Balanced Salt Solution (BSS) | Liquid | Similar in density, refractive index and transparency to vitreous | Temporary substitute No tamponade effect due to low surface tension |
| Perfluorocarbon Liquid (PFCL, PFD and PFO) | Liquid | High specific gravity, clear, colorless and odorless | Temporary substitute For intra-operative usage only Require complete removal Retinal toxicity, intraocular inflammatory reactions if retained |
| SiO | Liquid | Similar refractive index to vitreous Current gold standard for long-term tamponade (6 months) | Non-biodegradable Requires a second surgery for removal Cataract induction, corneal toxicity (band-K), glaucoma, macular oedema and "silicone retinopathy" |

While many materials have been proposed and tested, an ideal vitreous substitute remains elusive.

Although polymeric hydrogels such as currently available hydrogels (including gelatin, poly(1-vinyl-2-pyrrolidinone), polyvinylalcohol (PVA), polyacrylamide (PAA), tetra-arm poly(ethylene glycol) (Tetra-PEG)), cross-linked hyaluronic acid or self-assembling peptide gels are potential vitreous substitutes because they resemble natural vitreous humor, there are several limitations that prevent their usage as vitreous tamponade. Their limitations include (i) the inability of preformed polymeric hydrogels to maintain their tensile strength after injection through small bore needles, (ii) rapid biodegradability (i.e. short residence time), which prevents formation of chorio-retinal adhesions around retinal tears, and (iii) poor biocompatibility leading to severe intraocular inflammation and long-term toxicity. Often, their ability to exert sufficient surface tension across retinal breaks has either not been assessed or has been found lacking. For example, some commercially available hydrogels have shown that they tend to drift under the retinal tear, resulting in re-detachment of the retina.

In view of the above, there is a need to address or at least ameliorate the above-mentioned problems. In particular, there is a need for a material that is suitable for use as a vitreous humour substitute, a method of making the material and a synthetic vitreous humour that address or at least ameliorate the above-mentioned problems.

SUMMARY

In one aspect, there is provided a material comprising a multi-block thermogelling polymer, said multi-block thermogelling polymer comprising a hydrophilic polymer block; a thermosensitive polymer block; and a hydrophobic polymer block, wherein the hydrophilic polymer block, the thermosensitive polymer block and the hydrophobic polymer block are chemically coupled together by at least one of urethane/carbamate, carbonate, ester linkages or combinations thereof, and wherein the material is suitable for use as a vitreous substitute.

In one embodiment, the hydrophilic polymer block and the thermosensitive polymer block each comprises a poly(alkylene glycol).

In one embodiment, the poly(alkylene glycol) of the hydrophilic polymer block is different from the poly(alkylene glycol) of the thermosensitive polymer block.

In one embodiment, the hydrophilic polymer block comprises poly(ethylene glycol) and the thermosensitive polymer block comprises poly(propylene glycol).

In one embodiment, the hydrophobic polymer block comprises a polyester.

In one embodiment, the hydrophobic polymer block comprises a poly(caprolactone).

In one embodiment, the molar ratio of the hydrophilic polymer block to the thermosensitive polymer block is in the range of 1:1 to 10:1.

In one embodiment, the hydrophobic polymer block is in an amount of from 1 wt % to 10 wt % of the multi-block thermogelling polymer.

In one embodiment, the material comprises 1% to 30% w/v of the multi-block thermogelling polymer in an aqueous medium.

In one embodiment, the material has a high water content of more than 60% by weight.

In one embodiment, the material has a pH value in a range of from 7.1 to 7.7.

In one embodiment, the material is in a flowable state at a temperature falling in the range of 20° C. to 30° C. and is in a non-flowable gel-like state at a temperature falling in the range of 36° C. to 40° C.

In one embodiment, the material is substantially transparent.

In one embodiment, the material has a refractive index falling in the range of from 1.20 to 1.48.

In one embodiment, the biomaterial is substantially devoid of a metal.

In one aspect, there is provided a method of preparing a material disclosed herein, the method comprising: coupling one or more hydrophilic polymer, one or more thermosensitive polymer and one or more hydrophobic polymer together such that the hydrophilic polymer block, the thermosensitive polymer block and the hydrophobic polymer block are chemically coupled together by at least one of urethane/carbamate, carbonate, ester linkages or combinations thereof to form a multi-block polymer.

In one embodiment, the one or more hydrophilic blocks, one or more thermosensitive blocks and one or more hydrophobic blocks are mixed in a molar ratio of 1-10:1:0.01-1.5.

In one embodiment, the mixing step is performed at an elevated temperature in the range of from 70° C. to 150° C.

In one embodiment, the mixing step is carried out for at least 12 hours.

In one embodiment, the coupling step is carried out in the presence of a coupling agent and the coupling agent comprises an isocyanate monomer that contains at least two isocyanate functional groups.

In one embodiment, the coupling agent is a diisocyanate selected from the group consisting of hexamethylene diisocyanate, tetramethylene diisocyanate, cyclohexane diisocyanate, tetramethylxylene diisocyanate, dodecylene diisocyanate, tolylene 2,4-diisocyanate and tolylene 2,6-diisocyanate.

In one embodiment, the coupling step is carried out in the presence of an anhydrous solvent selected from the group consisting of toluene, benzene and xylene.

In one embodiment, the coupling step is carried out in the presence of a tin catalyst selected from the group consisting of alkyltin compounds, aryltin compounds and dialkyltin diesters.

In one embodiment, the method further comprises removing the multi-block polymer of contaminants; and solubilizing the multi-block polymer in aqueous medium to form a multi-block thermogelling polymer.

In one aspect, there is provided a synthetic vitreous humour or part thereof comprising the material disclosed herein.

Definitions

The term "biomaterial" refers broadly to a substance that has been engineered to interact with biological systems, whether alone or as part of a complex system. The biomaterial may be used for a medical purpose, for example, either a therapeutic (treat, augment, repair or replace a tissue function of the body) or a diagnostic one. A biomaterial may be natural or synthetic, alive or lifeless, and may be made of multiple components.

The term "substantially transparent" when used herein to describe an object is to be interpreted broadly to mean that 50% or more of the incident light normal to surface of the object can be transmitted through the object. In some examples, the object that is substantially transparent to light allow 60% or more, 65% or more, 70% or more, 80% or more, 85% or more, 90% or more or 95% or more of the incident light normal to surface of the object to be transmitted. In one example, the object that is substantially transparent to light allow above 70% of the incident light normal to surface of the object to be transmitted.

The terms "coupled" or "connected" as used in this description are intended to cover both directly connected or connected through one or more intermediate means, unless otherwise stated.

The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DESCRIPTION OF EMBODIMENTS

Exemplary, non-limiting embodiments of a material suitable for use as a vitreous humour substitute, a method of preparing the material, a synthetic vitreous humour and related methods are disclosed hereinafter.

There is provided a material comprising a multi-block polymer. The material may be a biomaterial. In various embodiments, the material comprises a biodegradable water-based biomaterial. Advantageously, in various embodiments, the material may be suitable for and/or fulfils the clinical requirements for use as a vitreous substitute/replacement biomimetic/synthetic vitreous humour and/or tamponading agent as well as in methods of treating disorders of the eye. For example, the material may serve as a surgical adjunct to treat ophthalmological disorders and to replace the vitreous humour of the eye. In various embodiments, the material overcomes or at least ameliorates one or more of the inherent issues of conventional preformed hydrogels as described above.

In various embodiments, the multi-block polymer is a multi-block copolymer. In some embodiments, the multi-block polymer is a tri-component multi-block polymer. For example, the multi-block polymer may have or is made up of three different polymer blocks. In some embodiments, the multi-block copolymer comprises more than three polymeric blocks. The multi-block polymer may be a thermosensitive, thermogelling and/or thermoreversible polymer. In various embodiments, the multi-block polymer functions as a hydrogel for use as a vitreous substitute.

In various embodiments, the multi-block polymer is a polymer that is not cross-linked or is a non-cross-linking/non-cross-linked/non-crosslinkable polymer. Advantageously, in various embodiments, preparation/formation of the material/polymers/gels disclosed herein does not require use of any additional crosslinkers. Such advantageous effects are not achievable by known methods such as those using naturally-derived poly(hydroxybutyrate) (PHB). It will be appreciated that in such known methods, ring opening synthesis is thermodynamically challenging and inaccessible to molecules.

In various embodiments, the material or multi-block polymer is in an amorphous state/non-crystalline. This is in contrast to polymers that are synthesized by known methods using for example poly(hydroxybutyrate), which contain physical crosslinking as a result of a crystallisation effect.

In various embodiments, the multi-block polymer comprises a hydrophilic polymer block; a thermosensitive polymer block; and a hydrophobic polymer block. The multi-block polymer may have at least one unit of the following structural sequence A-B-C, where A comprises the hydrophilic polymer block, B comprises the thermosensitive polymer block and C comprises the hydrophobic polymer block. It may be appreciated that in some embodiments, the positions of A, B and C may be interchanged among themselves. In various embodiments, the multi-block polymer may comprise a plurality of hydrophilic polymer blocks, a plurality of thermosensitive polymer blocks and/or a plurality of hydrophobic polymer blocks. In various embodiments, the multi-block copolymer comprises more than 3 polymeric blocks. The blocks may be randomly distributed/arranged within the polymer.

In various embodiments, the hydrophilic polymer block, the thermosensitive polymer block and the hydrophobic polymer block are chemically coupled together by at least one of urethane/carbamate, carbonate, ester linkages or combinations thereof. For example, each of the hydrophilic polymer block, the thermosensitive polymer block and the hydrophobic polymer block are linked to their respective adjacent block by at least one of urethane/carbamate, carbonate, ester linkages or combinations thereof.

In various embodiments, the hydrophilic polymer block and the thermosensitive polymer block each comprises a poly(alkylene glycol). In various embodiments, the poly(alkylene glycol) of the hydrophilic polymer block is different from the poly(alkylene glycol) of the thermosensitive polymer block. For example, the hydrophilic polymer block may comprise poly(ethylene glycol) while the thermosensitive polymer block may comprise poly(propylene glycol).

In various embodiments, the hydrophobic polymer block comprises a polyester such as a poly(caprolactone) (e.g. poly(ε-caprolactone)). Advantageously, in various embodiments, the use of polycaprolactone (PCL) allows for flexibility in the synthesis of the presently disclosed polymer. For example, using polycaprolactone in the synthesis of the presently disclosed multi-block polymer allows for the incorporation of molecules with the hydroxyl handle/functionality during the initial polymerisation step of PCL.

In various embodiments, the molar ratio of the hydrophilic polymer block to the thermosensitive polymer block is in the range of from about 1:1 to about 10:1. The molar ratio of the hydrophilic polymer block to the thermosensitive polymer block may be about 1:1, about 2:1, about 3:1, about 4:1, about 5:1, about 6:1, about 7:1, about 8:1, about 9:1 or about 10:1. In various embodiments, the hydrophobic polymer block is in an amount/concentration of from about 1 wt % to about 10 wt % of the multi-block polymer. The hydrophobic polymer block may be in an amount/concentration of about 1 wt %, about 2 wt %, about 3 wt %, about 4 wt %, about 5 wt %, about 6 wt %, about 7 wt %, about 8 wt %, about 9 wt %, or about 10 wt % of the multi-block polymer. In some embodiments, the multi-block polymer contains about 1 wt % of poly(caprolactone). In various embodiments, the molar ratio of hydrophilic block to thermosensitive block to hydrophobic block in the polymer is in the range of about 1-10: about 1: about 0.01-1.5.

In various embodiments, the material comprises/consists essentially of/consists of the multi-block polymer disclosed herein and water/aqueous medium/aqueous buffer. Accordingly, the material may exist as a composition or a formulation. In various embodiments, the material comprises about 1% to about 30% w/v of the multi-block thermogelling polymer in an aqueous medium. The aqueous medium may be a balanced salt solution. In various embodiments, the balanced salt solution is a solution having a physiological pH and isotonic salt concentration. In various embodiments, the balanced salt solution comprises at least one of sodium, potassium, calcium and magnesium salts such as calcium chloride, potassium chloride, magnesium chloride, sodium acetate, sodium citrate and sodium chloride. In various embodiments, the material comprises up to about 30% w/v of polymer in water/aqueous solution/buffer solution, or from about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, about 20% w/v, about 21% w/v, about 22% w/v, about 23% w/v, about 24% w/v, about 25% w/v, about 26% w/v, about 27% w/v, about 28% w/v, about 29% w/v, or about 30% w/v of polymer in water/aqueous solution/buffer solution. In various embodiments, the material comprises up to about 30 wt % of polymer in water/aqueous solution/buffer solution, or from about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, or about 30 wt % of polymer in water/aqueous solution/buffer solution. In some embodiments, the material has a specific concentration of about 7 to about 10% molecular weight. Advantageously, controlling the specific concentration of the polymer in accordance to various embodiments disclosed herein is believed to achieve a thermogel that has low toxicity to cells (usually toxicity will be a problem if specific concentration is extremely low) and low risk of high intraocular pressure in the eye (usually risk of high intraocular pressure occurs if the specific concentration is excessively high).

The material may have a high water content of more than about 60%, about 65%, about 70%, about 75%, about 80%, about 85%, about 90%, about 95%, about 96%, about 97%, about 98%, or about 99% by weight. Accordingly, the material may be a water-based polymer.

In various embodiments, the composition has a pH value that is substantially similar to physiological pH value ranging from about pH 7.1 to about pH 7.7, from about pH 7.2 to about pH 7.6, from about pH 7.3 to about pH 7.5, or about pH 7.4.

In various embodiments, the material has a critical gelation temperature/thermo-reversible sol-gel transition temperature/converts from a liquid/flowable state to a non-flowable/gel-like state at a temperature that is no less than about 33° C., no less than about 34° C., no less than about 35° C., no less than about 36° C., no less than about 36.5° C., no less than about 37° C., no less than about 37.5° C., no less than about 38° C., no less than about 38.5° C., no less than about 39.0° C., no less than about 39.5° C., no less than about 40° C., up to about 40° C. or at a temperature that is substantially similar to living human body temperature ranging from about 36.5° C. to about 37.5° C., or at about 37° C. For example, the material may be in a liquid/flowable state at ambient room temperature (e.g. about 20° C. to about 30° C.) and/or is in a non-flowable/gel-like state at living human body temperature (e.g. about 36° C. to about 40° C.). Therefore, in some embodiments, the material is in a flowable state at a temperature falling in the range of 20° C. to 30° C. and is in a non-flowable gel-like state at a temperature falling in the range of 36° C. to 40° C. Advantageously, in various embodiments, the material is deliverable as a liquid at 25° C. (viscosity of about 1 Pas) and gel at about 37° C. (viscosity range of about 8 Pas to about 110 Pas). Even more advantageously, the material may be introduced into the eye by injection in a liquid form to form a gel in the eye to replace the vitreous post-surgery. That is, in various embodiments, the material which may be a liquid at the time of injection may rapidly form a gel upon contact with the intra-ocular cavity at e.g. 37° C. to maintain the shape of the eye, and to provide an internal tamponading effect.

In various embodiments, the material has a critical gelation concentration of up to about 30 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, about 20 wt %, about 21 wt %, about 22 wt %, about 23 wt %, about 24 wt %, about 25 wt %, about 26 wt %, about 27 wt %, about 28 wt %, about 29 wt %, or about 30 wt % at a temperature of from about 30° C. to about 40° C.

In some embodiments, the conversion from a liquid/flowable state to a gel-like state is reversible e.g. through an application of an external force to convert the gel-like state back to the liquid/flowable state. For example, in various embodiments, the gel can be deformed into a liquid-state, from which it transits back to its original state instantaneously upon removal of the external force. Advantageously, this allows for effortless and swift injection through a narrow bore needle while retaining its structure and tensile strength, without compromising either viscosity or surface tension properties, and allows reformation of gel in-situ after injection.

In various embodiments, the material is substantially transparent and/or exhibits a high degree of optical clarity and/or a refractive index substantially similar to that of naturally occurring vitreous humour (e.g. at body temperature), such as from about 1.20 to about 1.48, from about 1.21 to about 1.47, from about 1.22 to about 1.46, from about 1.23 to about 1.45, from about 1.24 to about 1.44, from about 1.25 to about 1.43, from about 1.26 to about 1.42, from about 1.27 to about 1.41, from about 1.28 to about 1.40, from about 1.29 to about 1.39, from about 1.30 to about 1.38, from about 1.31 to about 1.37, from about 1.32 to about 1.36, from about 1.33 to about 1.35, from about 1.339 to about 1.349, from about 1.338 to about 1.348, from about 1.337 to about 1.347, from about 1.336 to about 1.346, from about 1.335 to about 1.345, or from about 1.334 to about 1.344. Advantageously, this ensures good immediate post-operative vision.

In some embodiments, the material is substantially devoid of perfluorocarbon liquids (PFCLs) and/or expansile gases and/or silicone oil. In some embodiments, the material is substantially devoid of unreacted polymers and/or organic solvents and/or metals.

In various embodiments, the material or multi-block polymer is substantially devoid of heavy metals. For example, the material or multi-block polymer may be substantially devoid of antimony and/or arsenic and/or cadmium and/or cobalt and/or copper and/or lead and/or lithium and/or mercury and/or nickel and/or vanadium.

In various embodiments, the material or multi-block polymer is substantially devoid of solvent contaminants. For example, the material or multi-block polymer may be substantially devoid of benzene and/or carbon tetrachloride and/or 1,2-dichloroethane and/or 1,1-dichloroethene and/or 1,1,1-trichloroethane and/or acetonitrile and/or chlorobenzene and/or chloroform and/or cyclohexane and/or 1,2-dichloroethene and/or dichloromethane and/or 1,2-dimethoxyethane and/or N,N-dimethylacetamide and/or N,N-dimethylformamide and/or 1,4-dioxane and/or 2-ethoxyethanol and/or ethyleneglycol and/or formamide and/or hexane and/or methanol and/or 2-methoxyethanol and/or methylbutylketone and/or methylcyclohexane and/or N-methylpyrrolidone and/or nitromethane and/or pyridine and/or sulfolane and/or tetrahydrofuran and/or tetralin and/or toluene and/or 1,1,2-trichloroethene and/or xylene (m-, p-, o-isomers) and/or acetic acid and/or acetone and/or anisole and/or 1-butanol and/or 2-butanol and/or butyl acetate and/or tert-butylmethyl ether and/or cumene and/or dimethyl sulfoxide and/or ethanol and/or ethyl acetate and/or ethyl ether and/or ethyl formate and/or formic acid and/or heptane and/or isobutyl acetate and/or isopropyl acetate and/or methyl acetate and/or 3-methyl-1-butanol and/or methylethylketone and/or methylisobutylketone and/or 2-methyl-1-propanol and/or pentane and/or 1-pentanol and/or 1-propanol and/or 2-propanol and/or propyl acetate.

In various embodiments, the entire multi-block polymer or at least one or more of the blocks within the polymer or the material is/are biodegradable and/or can be broken down naturally. In some examples, all the polymeric blocks are biodegradable. Advantageously, in various embodiments, as the material or multi-block polymer is biodegradable, when it is inserted as a vitreous humour substitute in a patient in an operation, the patient does not require a second operation to remove the material or multi-block polymer.

In various embodiments, the material has a short residence time and/or is capable of being degraded naturally in the animal body within about 6 months, within about 5 months, within about 4 months, within about 3 months, or within about 2 months. In some embodiments, the material has a short residence time and/or is capable of being degraded naturally in the animal body in the time period of between about 2 months and about 6 months.

In various embodiments, the material is biocompatible and/or non-toxic and/or does not elicit an inflammatory or adverse immune response in the body of an animal or human, particularly in the eye of an animal or human.

The material may be capable of retaining its desirable mechanical/optical properties while remaining in the animal or human body for at least about 1 month, at least about 2 months, at least about 3 months, at least about 4 months, at least about 5 months, at least about 6 months, or up to about 6 months. In some embodiments, the material/multi-block polymer or composition is capable of retaining its desirable mechanical/optical properties as long as the material/multi-block polymer or composition remains in the animal or human body.

In various embodiments, the material is capable of maintaining its tensile strength/mechanical viability even after being subjected to a stress over three orders of magnitude (for example at a stress magnitude in the region of at least about 101 Pa, at least about 102 Pa or at least about 103 Pa). In some examples, the material does not macroscopically collapse/shear at high strain after injection through small bore needles that have a gauge size of at least about 20, at least about 21, at least about 22, at least about 23, at least about 24, at least about 25, at least about 26, at least about 27, at least about 28, at least about 29, at least about 30 or more than about 30. In various embodiments, the material is capable of exerting surface tension across retinal breaks such as from about 25 mN/m to about 275 mN/m, from about 30 mN/m to about 270 mN/m, from about 35 mN/m to about 265 mN/m, from about 40 mN/m to about 260 mN/m, from about 45 mN/m to about 255 mN/m, from about 50 mN/m to about 250 mN/m, from about 55 mN/m to about 245 mN/m, from about 60 mN/m to about 240 mN/m, from about 65 mN/m to about 235 mN/m, from about 70 mN/m to about 230 mN/m, from about 75 mN/m to about 225 mN/m, from about 80 mN/m to about 220 mN/m, from about 85 mN/m to about 215 mN/m, from about 90 mN/m to about 210 mN/m, from about 95 mN/m to about 205 mN/m, from about 100 mN/m to about 200 mN/m, from about 110 mN/m to about 190 mN/m, from about 120 mN/m to about 180 mN/m, from about 130 mN/m to about 170 mN/m, from about 140 mN/m to about 160 mN/m, or about 150 mN/m to sufficiently provide the necessary support to mitigate and/or prevent retinal detachment when the material is used as a vitreous substitute.

In various embodiments, the material has a viscosity of no more than about 5 Pas at ambient room temperature (e.g. about 20° C. to about 30° C.) and/or a viscosity of from about 5 Pas to about 120 Pas at living human body temperature (e.g. about 36° C. to about 40° C.). In some embodiments, the material has a viscosity of from about 1 Pa·s to about 1000 Pa·s, from about Pa·s to about 990 Pa·s, from about 20 Pa·s to about 980 Pa·s, from about Pa·s to about 970 Pa·s, from about 40 Pa·s to about 960 Pa·s, from about 50 Pa·s to about 950 Pa·s, from about 60 Pa·s to about 940 Pa·s, from about 70 Pa·s to about 930 Pa·s, from about 80 Pa·s to about 920 Pa·s, from about 90 Pa·s to about 910 Pa·s, from about 100 Pa·s to about 900 Pa·s, from about 200 Pa·s to about 800 Pa·s, from about 300 Pa·s to about 700 Pa·s, from about 400 Pa·s to about 600 Pa·s, or about 500 Pa·s over a temperature range of from about 20° C. to about 40° C.

In various embodiments, the material has a conductivity of from about 7 mS/cm to about 13 mS/cm, from about 8 mS/cm to about 12 mS/cm, from about 9 mS/cm to about 11 mS/cm, or about 10 mS/cm at ambient room temperature (e.g. about 20° C. to about 30° C.) and/or a conductivity of from about 10 mS/cm to about 15 mS/cm, from about 11 mS/cm to about 14 mS/cm, or from about 12 mS/cm to about 13 mS/cm at living human body temperature (e.g. about 36° C. to about 40° C.).

There is also provided a method of preparing a material disclosed herein, the method comprising coupling one or more hydrophilic polymer, one or more thermosensitive polymer and one or more hydrophobic polymer together such that the hydrophilic polymer block, the thermosensitive polymer block and the hydrophobic polymer block are chemically coupled together by at least one of urethane/carbamate, carbonate, ester linkages or combinations thereof to form a multi-block polymer.

In various embodiments, the coupling step comprises mixing one or more hydrophilic polymer, one or more thermosensitive polymer and one or more hydrophobic polymer with a coupling agent in the presence of a metal catalyst and a suitable solvent to form a multi-block polymer comprising a hydrophilic polymer block; a thermosensitive polymer block; and a hydrophobic polymer block, wherein the hydrophilic polymer block, the thermosensitive polymer block and the hydrophobic polymer block are chemically coupled together by at least one of urethane/carbamate, carbonate, ester linkages or combinations thereof.

In various embodiments, the starting materials used to prepare the material or multi-block polymer are medical grade starting materials.

In various embodiments, the one or more hydrophilic blocks, one or more thermosensitive blocks and one or more hydrophobic blocks are mixed in a molar ratio of about 1-10:1:0.01-1.5. For example, the molar ratio of the hydrophilic blocks to the thermosensitive blocks may be about 1:1, about 2:1, about 3:1, about 4:1, about 5:1, about 6:1, about 7:1, about 8:1, about 9:1 or about 10:1. The molar ratio of the thermosensitive blocks to the hydrophobic blocks may be about 1:0.01, about 1:0.02, about 1:0.03, about 1:0.04, about 1:0.05, about 1:0.06, about 1:0.07, about 1:0.08, about 1:0.09, about 1:0.1, about 1:0.2, about 1:0.3, about 1:0.4, about 1:0.5, about 1:0.6, about 1:0.7, about 1:0.8, about 1:0.9, about 1:1, about 1:1.1, about 1:1.2, about 1:1.3, about 1:1.4, or about 1:1.5. Advantageously, in various embodiments, the specific molar ratio of the polymer blocks disclosed herein imparts an overall property of biocompatibility to the multi-block polymer or material as a whole.

In some embodiments, the amount of coupling agent added is equivalent to the number of reactive groups in the composition.

In various embodiments, the coupling and/or mixing step is performed at an elevated temperature of from about 70° C. to about 150° C., from about 72° C. to about 148° C., 74° C. to about 146° C., from about 76° C. to about 144° C., from about 78° C. to about 142° C., from about 80° C. to about 140° C., from about 82° C. to about 138° C., from about 84° C. to about 136° C., from about 86° C. to about 134° C., from about 88° C. to about 132° C., from about 90° C. to about 130° C., from about 92° C. to about 128° C., from about 94° C. to about 126° C., or from about 96° C. to about 124° C., from about 98° C. to about 122° C., from about 100° C. to about 120° C., from about 102° C. to about 118° C., from about 104° C. to about 116° C., from about 106° C. to about 114° C., from about 108° C. to about 112° C., or about 110° C.

In various embodiments, the coupling and/or mixing step is carried out for at least about 12 hours, at least about 14 hours, at least about 16 hours, at least about 18 hours, at least about 20 hours, at least about 22 hours, at least about 24 hours, at least about 26 hours, at least about 28 hours, at least about 30 hours, at least about 32 hours, at least about 34 hours, at least about 36 hours, at least about 38 hours, at least about 40 hours, at least about 42 hours, at least about 44 hours, at least about 46 hours, or at least about 48 hours.

In various embodiments, the coupling and/or mixing step is performed in the absence of air and/or water/moisture and/or in the presence of an inert gas such as nitrogen.

In various embodiments, the coupling agent comprises an isocyanate monomer that contains at least two (two or more) isocyanate functional groups. The coupling agent may be a diisocyanate selected from the group consisting of hexamethylene diisocyanate, tetramethylene diisocyanate, cyclohexane diisocyanate, tetramethylxylene diisocyanate, dodecylene diisocyanate, tolylene 2,4-diisocyanate and tolylene 2,6-diisocyanate.

In various embodiments, the solvent comprises an anhydrous solvent selected from the group consisting of toluene, benzene and xylene.

In various embodiments, the metal catalyst comprises a tin catalyst selected from the group consisting of alkyltin compounds, aryltin compounds and dialkyltin diesters such as dibutyltin dilaurate, dibutyltin diacetate, dibutyltin dioctanoate and dibutyltin distearate.

In various embodiments, the method further comprises removing the multi-block polymer of/from contaminants; and solubilizing the multi-block polymer in aqueous medium to form a multi-block thermogelling polymer. The step of removing the multi-block polymer of/from contaminants may comprise purifying and/or washing the multi-block polymer. The step of solubilizing the multi-block polymer in aqueous medium may comprise redissolving the polymer (e.g. final polymer powder) in a balanced salt solution (BSS). In various embodiments, BSS is water-based.

In various embodiments, the step of removing the multi-block polymer of/from contaminants comprises dialysis to remove unreacted reactants, solvents and catalyst (e.g. extensive dialysis to remove unreacted PEG, solvents and metallic catalyst etc).

The method may also further comprise sterilizing the material for example by autoclaving methods or techniques.

There is also provided a synthetic vitreous humour or part thereof comprising the material disclosed herein.

There is also provided a biomimetic/synthetic vitreous humour/tamponading agent comprising the material disclosed herein in the form of a flowable/injectable composition/formulation that is suitable as a vitreous humour substitute.

There is also provided a material, polymer or flowable/injectable composition/formulation disclosed herein or biomimetic/synthetic vitreous humour/tamponading agent comprising said polymer/composition/formulation for use in medicine.

There is also provided a material, polymer or flowable/injectable composition/formulation or biomimetic/synthetic vitreous humour/tamponading agent disclosed herein for use in drug delivery in the eye, stem cell transplantations of the eye, for use in the prevention/prophylaxis of recurrent retinal detachment such as from proliferative vitreoretinopathy or for use in the prophylaxis or treatment of ophthalmological disorders/deteriorations of the eye such as retinal detachment, vitreous haemorrhage, epi-retinal membranes and macular holes.

There is also provided use of a material, polymer or flowable/injectable composition/formulation or biomimetic/synthetic vitreous humour/tamponading agent disclosed herein in the manufacture of a medicament for use in drug delivery in the eye, stem cell transplantation or in the manufacture of a medicament for the prevention/prophylaxis of recurrent retinal detachment such as from proliferative vitreoretinopathy or for the prophylaxis or treatment of ophthalmological disorders/deterioration of the eye such as retinal detachment, vitreous haemorrhage, epi-retinal membranes and macular holes.

There is also provided a method of preventing or treating ophthalmological disorders/deteriorations of the eye such as retinal detachment, recurrent retinal detachment, vitreous haemorrhage, epi-retinal membranes and macular holes, the method comprising administering/injecting/infusing/delivering a therapeutically effective amount of the material, polymer or flowable/injectable composition/formulation or biomimetic/synthetic vitreous humour/tamponading agent disclosed herein to a patient in need thereof.

There is also provided a method of treating ophthalmological disorders/deteriorations of the eye, the method comprising administering/injecting/infusing/delivering a therapeutically effective amount of the material, polymer or flowable/injectable composition/formulation or biomimetic/synthetic vitreous humour/tamponading agent disclosed herein to a subject/patient in need thereof, wherein the composition/polymer is capable of being resident in the eye and providing support for the retina until treatment is completed. Advantageously, in various embodiments, there is relative ease of use of the material or multi-block polymer during surgery (e.g. vitrectomy to treat ophthalmological disorders of the eye) as the material or multi-block polymer is able to inject well and there is substantially no shearing after injection through small bore needles (23-25G). Even more advantageously, the use of the material or multi-block polymer is capable of providing good immediate post-operative vision as it provides optical clarity and has a similar refractive index to naturally occurring/native vitreous humour.

In various embodiments, the method of preventing or treating ophthalmological disorders/deteriorations of the eye disclosed herein is devoid of the use of gas buoyancy to support the retina and/or devoid of the step of subsequently removing a part of the material, polymer or flowable/injectable composition/formulation or biomimetic/synthetic vitreous humour/tamponading agent from the eye, and/or subsequently positioning the patient/subject face down. Advantageously, in various embodiments, as the use of the material or multi-block polymer as a vitreous humour substitute does not rely on buoyancy to support the retina, there is no need for awkward face-down positioning of the patient post-operation.

In various embodiments, the material or multi-block polymer disclosed herein has one of more of the follow properties: (1) good transparency at body temperature (37° C.); (2) a refractive index of 1.339 to 1.344 (similar to native vitreous—1.337) due to its high (>90%) water content; (3) can be injected with ease whilst in sol-gel transition state at 25° C., and rapidly forming a gel in-situ within the vitreous cavity at 37° C.; (4) has sufficient surface tension and swelling counter force to generate sufficient surface tension to bridge across the site of retinal break and assist re-apposition of detached retina through exertion of swelling counter force (i.e. similar to silicone oil which is the clinical gold standard for long-term tamponade) without the need for post-operative face-down positioning; (5) is biocompatible for up to 6 months in rabbit vitrectomy models with normal intraocular pressure, maintenance of lens clarity, and normal retinal structure and function; (6) is able to maintain retinal attachment post retinal repair surgery in non-human primate models; (7) acts as a biodegradable scaffold for in-vivo restoration of the vitreous body which obviates the need for a second removal surgery.

BRIEF DESCRIPTION OF FIGURES

FIG. 22C shows H&E analysis of the macular of EPC-7% filled eye.

FIGS. 22D and 22E show overview of macular structure, with scale bar=50 µm.

FIG. 25A shows mass-spectrometry (MS) analysis of native vitreous. FIG. 25B shows mass-spectrometry (MS) analysis of native vitreous spiked in with EPC-7% polymer as a positive control. FIG. 25C shows mass-spectrometry (MS) analysis of fluid sampled from vitreous cavity of operated control at 3-months post operation. FIG. 25D shows mass-spectrometry (MS) analysis of vitreous-like body samples from vitreous cavity of EPC-7% filled at 3-months post-operation, indicating the absence of detectable EPC-7% polymer.

FIG. 26A shows $^1$H NMR spectra (in $CDCl_3$, 25° C.) of pure EPC-7% thermogel to serve as a control, Peaks "a to d" indicates presence of all PCL, PEG, PPG segments and isocyanate moieties. FIG. 26B shows $^1$H NMR spectra (in $CDCl_3$, 25° C.) of EPC-7% vitreous-like body at 2-month post-operation, indicating that EPC gel is still present as shown by the presence of all segments of the thermogel (i.e. PCL, PEG, PPG and isocyanate moieties). FIG. 26C shows $^1$H NMR spectra (in CDCl$_3$, 25° C.) of EPC-7% vitreous-like body at 3-months post-operation, indicating that EPC 7% gel is not detected at all (as shown by the absence of any peaks corresponding to "a, b, c or d"). *solvent impurity (acetone).

EXAMPLES

Figure 1:
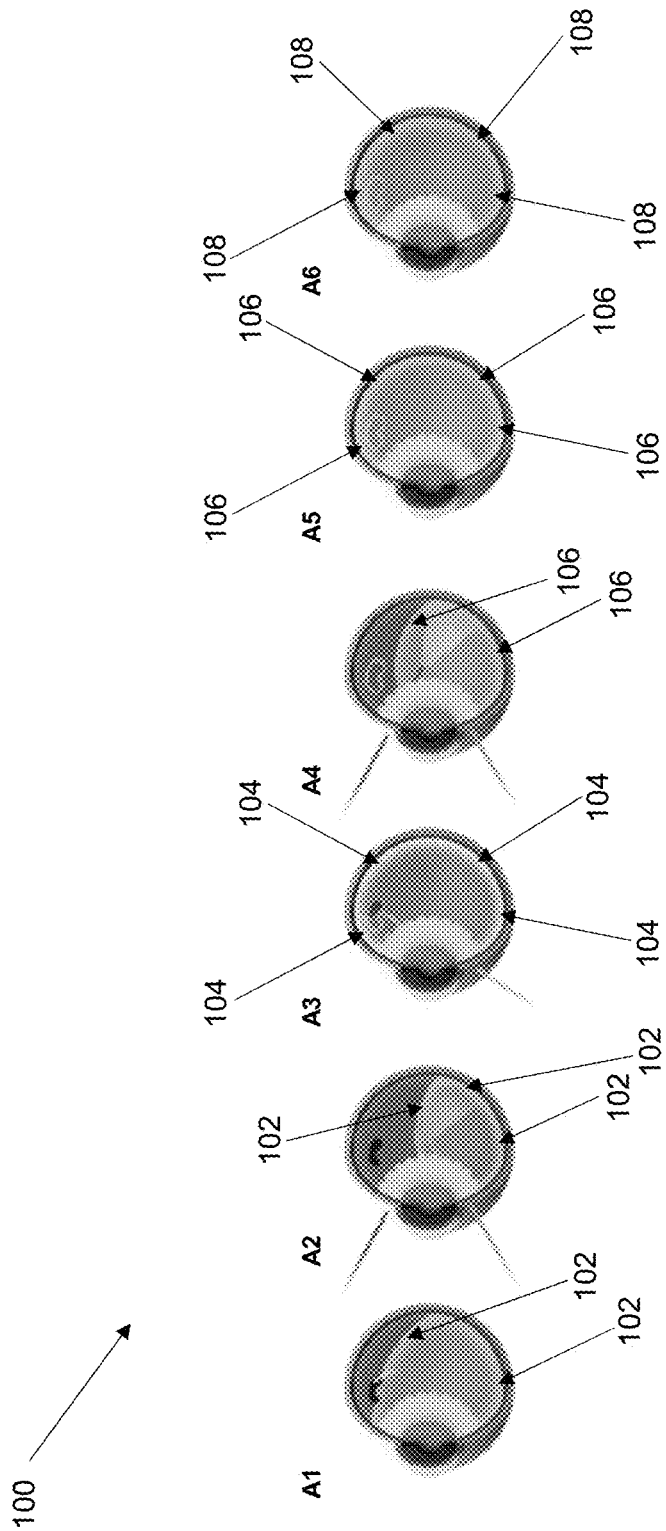
FIG. 1 is a schematic diagram 100 for illustrating the application of a polymer as a vitreous substitute in the clinical repair of retinal detachment in accordance with an example embodiment disclosed herein.

Example embodiments of the disclosure will be better understood and readily apparent to one of ordinary skill in the art from the following examples, tables and if applicable, in conjunction with the figures. It should be appreciated that other modifications related to structural, and chemical changes may be made without deviating from the scope of the invention. Example embodiments are not necessarily mutually exclusive as some may be combined with one or more embodiments to form new example embodiments. The example embodiments should not be construed as limiting the scope of the disclosure.

Example 1: Design and Application of Polymer

A chemical structure of an exemplary polymer designed in accordance with various embodiments disclosed herein is shown in Scheme 1. The polymer is a tri-component multi-block thermogelling polymer which consists of hydrophilic poly(ethylene glycol) (PEG), thermosensitive poly(propylene glycol) (PPG), and hydrophobic biodegradable polyesters such as, but not limited to, biodegradable poly(ε-caprolactone) (PCL) segments linked together via urethane bonds.

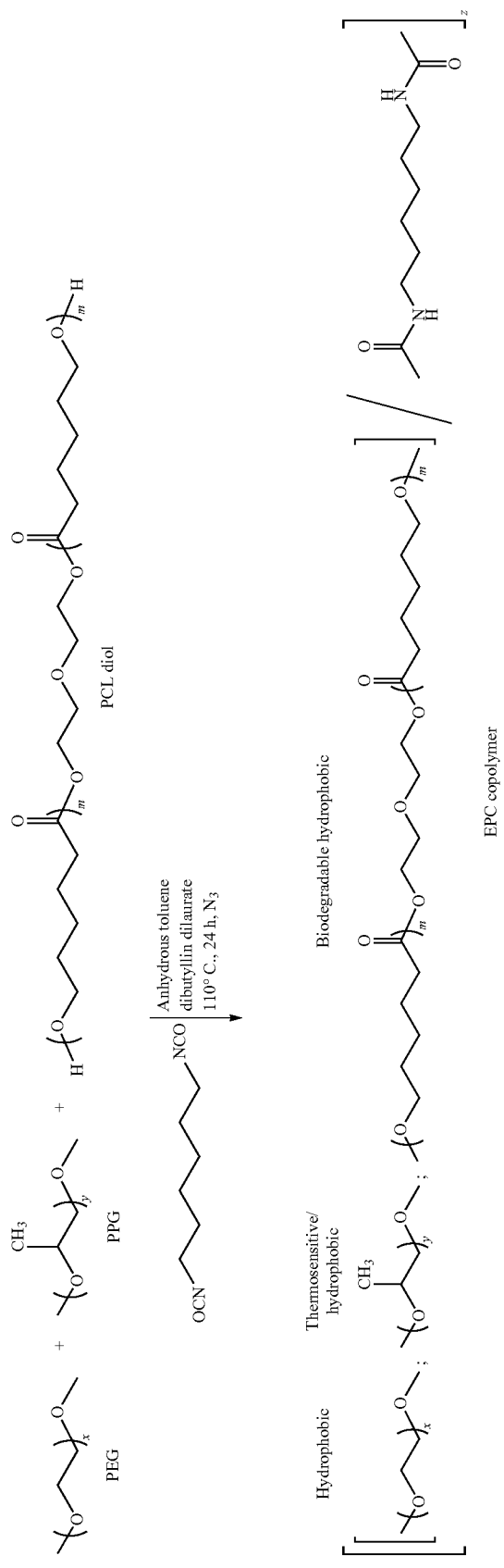
Scheme 1. Chemical structure and polymerisation of an exemplary polymer Synthesis of Polymer The general steps for preparing a polymer in accordance with various embodiments disclosed herein include: mixing one or more hydrophilic polymers, one or more hydrophobic polymers and one or more thermosensitive polymers with a coupling agent (in the example below, 1,6-diisocyanatohexane was used) in the presence of a metal catalyst (in the example below, dibutyltin dilaurate was used) and a suitable solvent (in the example below, toluene was used), as shown in Scheme 1.

An example of preparing a polymer designed in accordance with various embodiments disclosed herein is described in detail as follows.

Poly(PEG/PPG/PCL urethane) was synthesized from PEG, PPG, and PCL-diol using 1,6-Diisocyanatohexane as a coupling reagent. The amount of 1,6-Diisocyanatohexane added was equivalent to the reactive hydroxyl groups in the solution. Typically, 0.25 g of PCL-diol (Mn=2040, $1.23 \times 10^{-4}$ mol), 5 g of PEG (Mn=1890, $2.65 \times 10^{-3}$ mol), and 5 g of PPG (Mn=1880, $2.66 \times 10^{-3}$ mol) were dried in a 250-mL two-neck flask at 50° C. under high vacuum overnight. Then, 200 mL of anhydrous 1,2-toluene was added to the flask, and any trace of water in the system was removed through azeotropic distillation with only 40 mL of toluene being left in the flask. When the flask was cooled down to 75° C., 0.912 g of 1,6-Diisocyanatohexane ($5.43 \times 10^{-3}$ mol) and two drops of dibutyltin dilaurate ($\sim 8 \times 10^{-3}$ g) were added sequentially. The reaction mixture was stirred at 60-110° C. under a nitrogen atmosphere for 24-48 h. The resultant copolymer was precipitated from diethyl ether and further purified by re-dissolving into chloroform, followed by precipitation in a mixture of methanol and diethyl ether. The yield was 85% after isolation and purification.

Advantageously, the polymer designed in accordance with various embodiments disclosed herein rapidly forms a gel upon contact with the intra-ocular cavity at 37° C. Even more advantageously, as embodiments of the polymer disclosed herein gel inside the eye (or within the vitreous cavity), the polymer may be introduced into an eye vitreous cavity to be used as a surgical adjunct for treating ophthalmological disorders and to replace the vitreous. Embodiments of the polymer disclosed herein may therefore be used as vitreous substitute for maintaining the shape of the eye and provides an internal tamponading effect. They may be used as vitreous substitute for vitrectomy to treat ophthalmological disorders of the eye such as, but not limited to, retinal detachments, vitreous haemorrhage, epi-retinal membranes, macular holes and stem cell transplantations. In addition, embodiments of the polymer are capable of remaining in the eye for long periods of time (i.e 3 to 6 months) before biodegradation. Further, embodiments of the polymer are transparent and have the same refractive index as vitreous. Embodiments of the polymer disclosed herein are capable of providing physical support for the retina, and acts as an internal tamponade.

Importantly, as will be shown in the following examples, embodiments of the polymers/gels disclosed herein overcome the inherent issues of conventional preformed hydrogels in the art.

Application of Polymer as a Vitreous Substitute

FIG. 1 is a schematic diagram 100 for illustrating the application of a polymer as a vitreous substitute in the clinical repair of retinal detachment in accordance with an example embodiment disclosed herein.

(A1) of FIG. 1 shows retinal detachment with retinal tear. The vitreous is attached to anterior lip of retina tear causing traction. Native vitreous are represented by reference numeral 102. (A2) of FIG. 1 shows core vitrectomy (removal of vitreous). (A3) of FIG. 1 shows endolaser around retinal tear after air-fluid exchange. The air-filled vitreous cavity is indicated by reference numeral 104. (A4) of FIG. 1 shows injection of thermogel 106 in the eye to provide internal tamponade. (A5) of FIG. 1 shows that the thermogel 106 supports retina and allows chorio-retinal adhesion to occur at the site of retinal laser. (A6) of FIG. 1 shows that the thermogel is replaced by vitreous-like body 108 after biodegradation.

The gel is introduced into the eye as a liquid (by way of an injection) and is then allowed to gelate within the vitreous cavity, after a pars plana vitrectomy to remove residual vitreous, as well as retinal tractional bands. The retina is reattached by conventional means. The vitreous fluid will be replaced initially with air (fluid air exchange) followed by injecting the gel. These gels are biodegradable, and thus there is no need for a second surgery to remove them in the postoperative period. Because of the consistency of the gel and their softness, they provide gentle support for the retinal structure and prevent accumulation of fluid, cells and subsequent membrane formation, which is often seen with the use of silicone oil or other liquid materials (due to the dead spaces left between these materials and the retina).

Example 2: Polymer Development and Characterisation

The hydrogel designed in accordance with various embodiments disclosed herein was developed and characterized. The results obtained from the characterisation studies are provided as follows.

i) Oscillatory Stress Sweep Measurement

Figure 2:
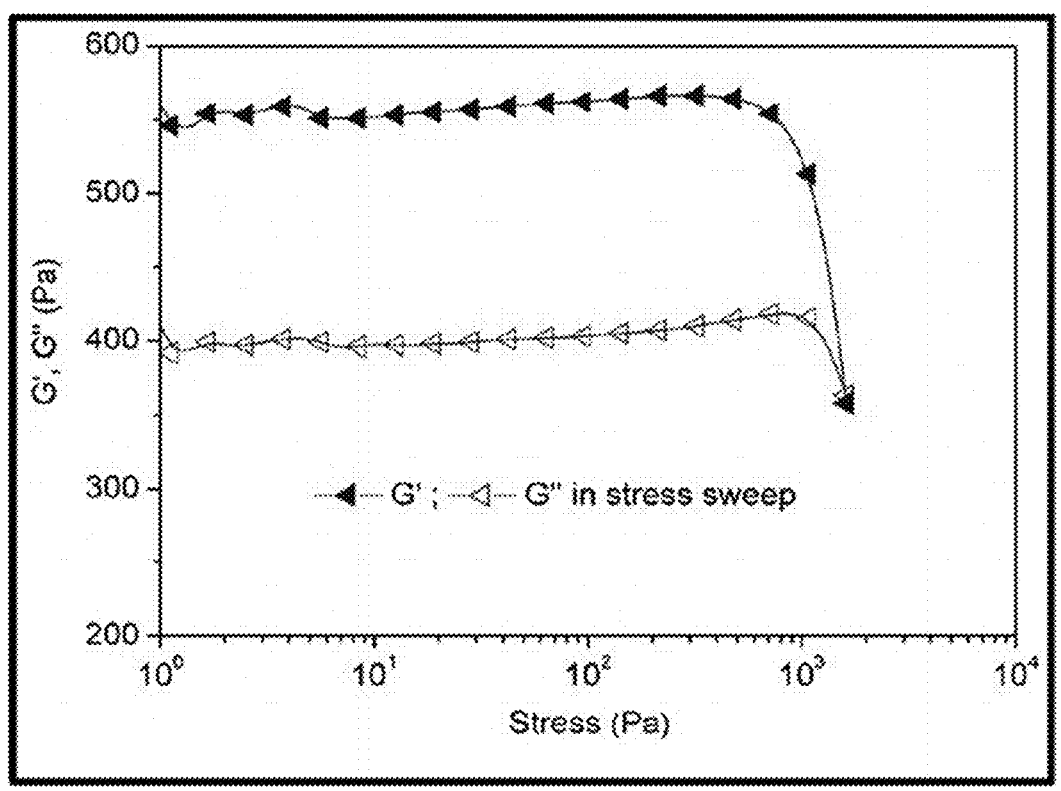
FIG. 2 is a graph showing the results obtained from oscillatory stress sweep measurement experiments performed on an exemplary hydrogel designed in accordance with various embodiments disclosed herein.

Oscillatory stress sweep measurement experiments were performed on an exemplary hydrogel designed in accordance with various embodiments disclosed herein and the results are provided in FIG. 2. As shown, the mechanical viability of the hydrogel can be maintained over 3 magnitudes order of stress.

ii) Dependence of Viscosity on Temperature and Polymer Concentration

Figure 3:
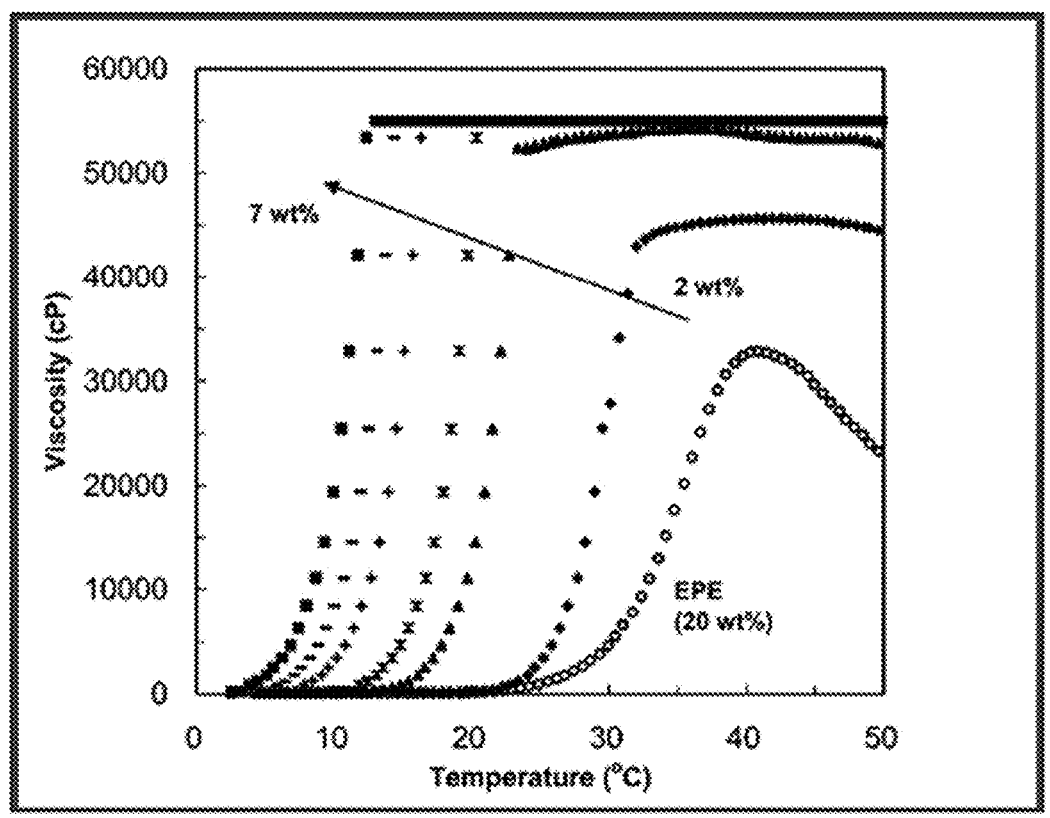
FIG. 3 is a graph showing the changes in the viscosity of an exemplary hydrogel designed in accordance with various embodiments disclosed herein with varying temperature and polymer concentration. The symbols (■) to (♦) represent the different concentrations of EPC polymer in balanced salt solution (BSS) ranging from 7 wt % to 2 wt %. EPC stands for PEG-PPG-PCL triblock polymer. For the EPC samples, the ratio of PEG:PPG is 4:1 and the concentration of PCL is 1 wt % of the polymer. The symbol (○) represents EPE, which stands for the PEG-PPG-PEG triblock polymer.

FIG. 3 shows the changes in the viscosity of an exemplary hydrogel designed in accordance with various embodiments disclosed herein with varying temperature and polymer concentration. As shown, viscosity can be tuned by (1) varying individual component ratios; or (2) varying polymer concentration in the solution.

iii) Mass Loss (%) of Hydrogels Measured at pH 7.4 and 37° C. (in BSS)

Figure 4:
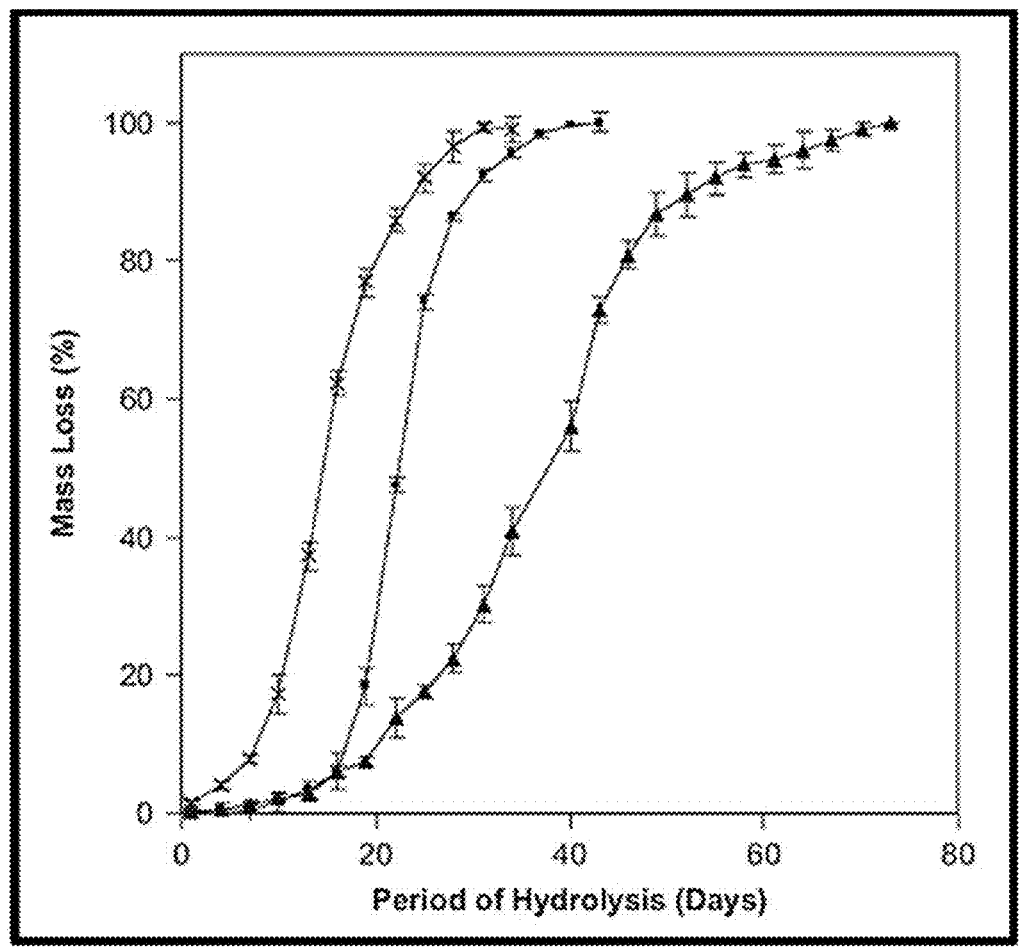
FIG. 4 is a graph showing the changes in the loss in mass (in %) of an exemplary hydrogel designed in accordance with various embodiments disclosed herein, as measured at pH 7.4 and 37° C. in a balanced salt solution (BSS). Cross (x) represents EPC3%, square (■) represents EPC7%, triangle (▲) represents EPC12%.

FIG. 4 shows the changes in mass loss (in %) of an exemplary hydrogel designed in accordance with various embodiments disclosed herein, as measured at pH 7.4 and 37° C. in a balanced salt solution (BSS). Degradation time can be varied to fit any specific clinical applications. For example, the hydrogel may be designed and developed as a short-term, medium-term or long-term tamponade for retinal detachment (RD) repair.

iv) Surface Tension of Thermogelling Solutions

Figure 5:
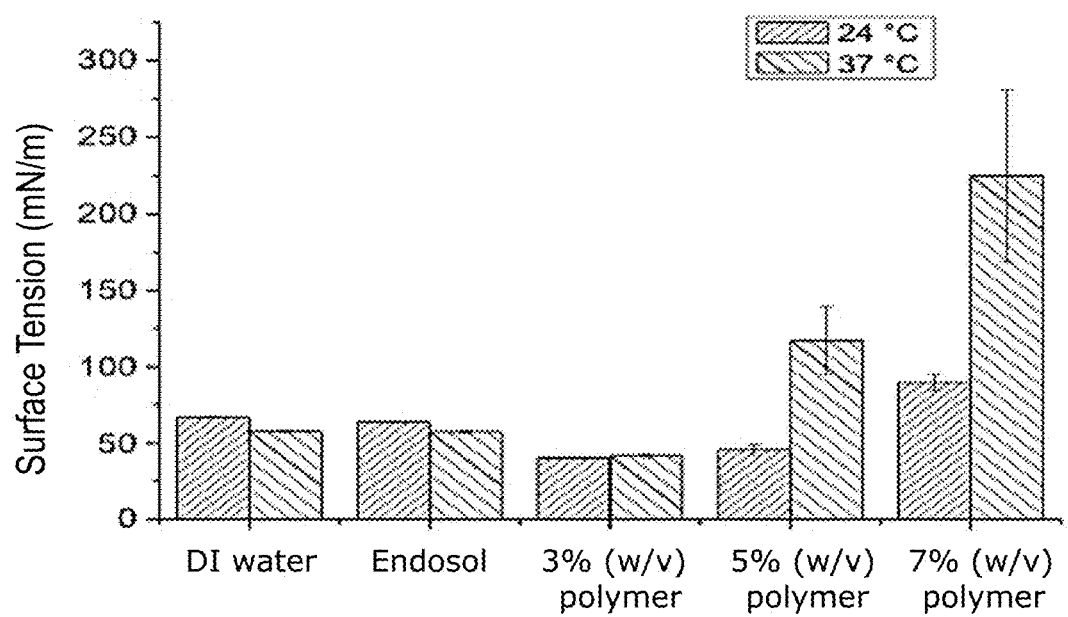
FIG. 5 is a graph showing the surface tension of thermogelling solutions having 3% (w/v), 5% (w/v) and 7% (w/v) of gel in water measured at specific temperatures of 24° C. and 37° C. respectively. In the thermogelling solutions, the ratio of PEG:PPG is 4:1 and the concentration of PCL is 1 wt % of the polymer.

Surface tension of thermogelling solutions having 3% (w/v), 5% (w/v) and 7% (w/v) of gel in water were measured respectively with a tensiometer which was equipped with DuNouy ring, at specific temperatures of 24° C. and 37° C. respectively. In the thermogelling solutions, the ratio of PEG:PPG is 4:1 and the concentration of PCL is 1 wt % of the polymer. The results are shown in FIG. 5.

v) Viscosity Temperature Ramp

Figure 6:
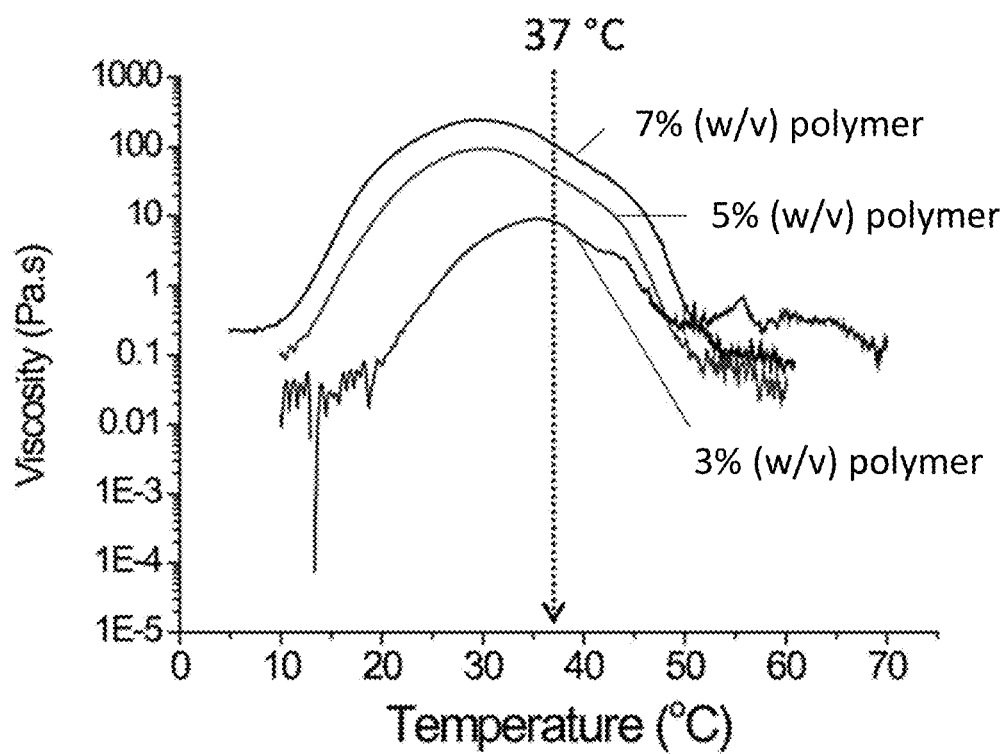
FIG. 6 is a graph showing the changes in the viscosity of thermogelling solutions having 3% (w/v), 5% (w/v) and 7% (w/v) of gel in water with varying temperature, measured at a shear rate=1.25 $s^{-1}$ and temperature ramp rate=3° C./min. In the thermogelling aqueous solutions, the ratio of PEG:PPG is 4:1 and the concentration of PCL is 1 wt % of the polymer.

FIG. 6 shows the changes in the viscosity of thermogelling solutions having 3% (w/v), 5% (w/v) and 7% (w/v) of gel in water with varying temperature, measured at a shear rate=1.25 s$^{-1}$ and temperature ramp rate=3° C./min. In the thermogelling aqueous solutions, the ratio of PEG:PPG is 4:1 and the concentration of PCL is 1 wt % of the polymer.

As shown, the viscosity of the thermogelling solutions at 37° C. for 3% (w/v) polymer is 8.3 Pa·s, the viscosity of the thermogelling solutions at 37° C. for 5% (w/v) polymer is 38.8 Pa·s, and the viscosity of the thermogelling solutions at 37° C. for 7% (w/v) polymer is 107 Pa·s.

vi) Conductivity of Thermogelling Solutions

Figure 7:
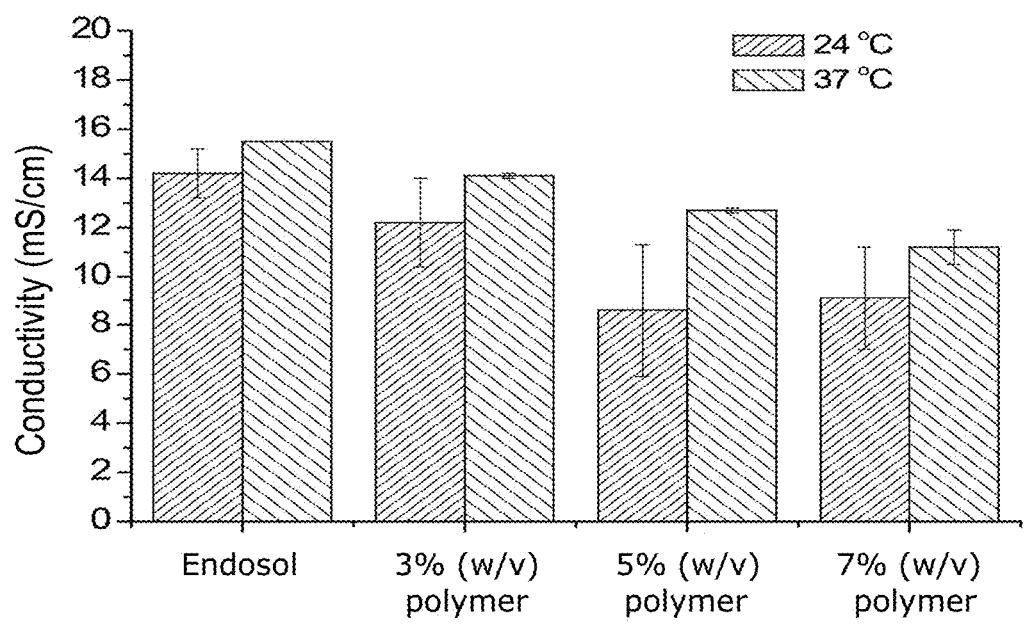
FIG. 7 is a graph showing the conductivity of thermogelling solutions having 3% (w/v), 5% (w/v) and 7% (w/v) of gel in water measured respectively after pH adjustment (7.2-7.3), at specific temperatures of 24° C. and 37° C. respectively. The pH of the endosol buffer is 7.6. In the thermogelling solutions, the ratio of PEG:PPG is 4:1 and the concentration of PCL is 1 wt % of the polymer.

Conductivity of thermogelling solutions having 3% (w/v), 5% (w/v) and 7% (w/v) of gel in water were measured respectively after pH adjustment (7.2-7.3), at specific temperatures of 24° C. and 37° C. respectively. The pH of the endosol buffer is 7.6. In the thermogelling solutions, the ratio of PEG:PPG is 4:1 and the concentration of PCL is 1 wt % of the polymer. The results are shown in FIG. 7.

vii) Temperature Ramp

The temperature dependence of thermogelling solutions having 3% (w/v), 5% (w/v) and 7% (w/v) of gel in water was measured at strain=1%, frequency=1 Hz and temperature ramp rate=3° C./min. In the thermogelling aqueous solutions, the ratio of PEG:PPG is 4:1 and the concentration of PCL is 1 wt % of the polymer.

For 3% (w/v) polymer, the modulus crossover mod is about 3.018 Pa, temperature is about 27.7° C. and G' at 37° C. is 8.2 Pa. For 5% (w/v) polymer, the modulus crossover mod is about 11.64 Pa, temperature is about 18.8° C. and G' at 37° C. is 184 Pa. For 7% (w/v) polymer, the modulus crossover mod is about 14.79 Pa, temperature is about 16.3° C. and G' at 37° C. is 448 Pa. As can be seen, increasing the concentration of polymer in the solution resulted in higher gel storage modulus at 37° C.

viii) Strain Amplitude Sweep

Strain amplitude sweep experiments were performed on thermogelling solutions having 3% (w/v), 5% (w/v) and 7% (w/v) of gel in water, at specific temperatures of 25° C. and 37° C. respectively. In the thermogelling aqueous solutions, the ratio of PEG:PPG is 4:1 and the concentration of PCL is 1 wt % of the polymer.

The thermogelling solutions at different concentrations were not affected by change in strain even in large amplitude oscillation of 10%-100%, therefore indicating that the hydrogel designed in accordance with various embodiments disclosed herein is a stable gel without macroscopic collapse at high strain.

ix) Frequency Sweep

Frequency sweep experiments were performed on thermogelling solutions having 3% (w/v), 5% (w/v) and 7% (w/v) of gel in water, at specific temperatures of 25° C. and 37° C. respectively. In the thermogelling aqueous solutions, the ratio of PEG:PPG is 4:1 and the concentration of PCL is 1 wt % of the polymer.

x) Elemental Analysis Using Inductively Coupled Plasma Mass Spectrometry

Samples of 10 wt % polymer were sent to TUV SOD PSB Pte. Ltd. for Inductively Coupled Plasma Mass Spectrometry (ICP-MS) analysis. The sample was dissolved in water, followed by elemental analysis using ICP-MS. Table 2 shows the ICP-MS results provided by TUV SOD.

TABLE 2

Elemental Analytical Results for 10 wt % polymer

| Test | Result | Permitted Parenteral Concentration (µg/g)$^b$ | Inferred Result |
|---|---|---|---|
| Antimony, Sb | Not Detected $^a$ | 9 | Pass |
| Arsenic, As | 0.005 | 1.5 | Pass |
| Cadmium, Cd | Not Detected $^a$ | 0.2 | Pass |
| Cobalt, Co | Not Detected $^a$ | 0.5 | Pass |
| Copper, Cu | 0.02 | 30 | Pass |
| Lead, Pb | Not Detected $^a$ | 0.5 | Pass |
| Lithium, Li | Not Detected $^a$ | 25 | Pass |
| Mercury, Hg | Not Detected $^a$ | 0.3 | Pass |
| Nickel, Ni | Not Detected $^a$ | 2 | Pass |
| Vanadium, V | Not Detected $^a$ | 1 | Pass |

$^a$ The method detection limit was 0.0001 ppm (1 µg/g = 1 ppm).
$^b$The permitted concentration limits of elements across drug product companies for drug products with daily intakes of not more than 10 grams.
Note:
The elements for the leachable test were selected for the parenteral assessment with reference to FDA Q3D Elemental Impurities Guidance for Industry.

Results indicated a lack of heavy metals in the polymer developed in accordance with various embodiments disclosed herein.

xi) Organic Residual Solvent Test

Samples of 10 wt % polymer were sent to TUV SOD PSB Pte Ltd for organic residual solvent test. Approximately 1 gram of sample was sealed in a 20 ml glass vial and heated at 90° C. for 20 minutes before being analysed by Headspace-Gas Chromatograph with Flame Ionisation Detector (GC-FID). Table 3 shows the GC-FID results provided by TUV SOD.

TABLE 3

Analytical Results for 10 wt % polymer

| Residual Solvent* | Components | Results (ppm) |
|---|---|---|
| Class 1 | benzene | Not Detected $^a$ |
| Class 1 | carbon tetrachloride | Not Detected $^a$ |
| Class 1 | 1,2-dichloroethane | Not Detected $^b$ |
| Class 1 | 1,1-dichloroethene | Not Detected $^b$ |
| Class 1 | 1,1,1-trichloroethane | Not Detected $^b$ |
| Class 2 | acetonitrile | Not Detected $^c$ |
| Class 2 | chlorobenzene | Not Detected $^c$ |
| Class 2 | chloroform | Not Detected $^c$ |
| Class 2 | cyclohexane | Not Detected $^c$ |
| Class 2 | 1,2-dichloroethene | Not Detected $^c$ |
| Class 2 | dichloromethane | Not Detected $^c$ |
| Class 2 | 1,2-dimethoxyethane | Not Detected $^c$ |
| Class 2 | N,N-dimethylacetamide | Not Detected $^c$ |
| Class 2 | N,N-dimethylformamide | Not Detected $^c$ |
| Class 2 | 1,4-dioxane | Not Detected $^c$ |
| Class 2 | 2-ethoxyethanol | Not Detected $^c$ |
| Class 2 | ethyleneglycol | Not Detected $^c$ |
| Class 2 | formamide | Not Detected $^c$ |
| Class 2 | hexane | Not Detected $^c$ |
| Class 2 | methanol | Not Detected $^c$ |
| Class 2 | 2-methoxyethanol | Not Detected $^c$ |
| Class 2 | methylbutylketone | Not Detected $^c$ |
| Class 2 | methylcyclohexane | Not Detected $^c$ |
| Class 2 | N-methylpyrrolidone | Not Detected $^c$ |
| Class 2 | nitromethane | Not Detected $^c$ |
| Class 2 | pyridine | Not Detected $^c$ |
| Class 2 | sulfolane | Not Detected $^c$ |
| Class 2 | tetrahydrofuran | Not Detected $^c$ |
| Class 2 | tetralin | Not Detected $^c$ |
| Class 2 | toluene | Not Detected $^c$ |
| Class 2 | 1,1,2-trichloroethene | Not Detected $^c$ |
| Class 2 | xylene (m-, p-, o-isomers) | Not Detected $^c$ |
| Class 3 | acetic acid | Not Detected $^c$ |
| Class 3 | acetone | Not Detected $^c$ |
| Class 3 | anisole | Not Detected $^c$ |
| Class 3 | 1-butanol | Not Detected $^c$ |
| Class 3 | 2-butanol | Not Detected $^c$ |

TABLE 3-continued

Analytical Results for 10 wt % polymer

| Residual Solvent* | Components | Results (ppm) |
|---|---|---|
| Class 3 | butyl acetate | Not Detected [c] |
| Class 3 | tert-butylmethyl ether | Not Detected [c] |
| Class 3 | cumene | Not Detected [c] |
| Class 3 | dimethyl sulfoxide | Not Detected [c] |
| Class 3 | ethanol | Not Detected [c] |
| Class 3 | ethyl acetate | Not Detected [c] |
| Class 3 | ethyl ether | Not Detected [c] |
| Class 3 | ethyl formate | Not Detected [c] |
| Class 3 | formic acid | Not Detected [c] |
| Class 3 | heptane | Not Detected [c] |
| Class 3 | isobutyl acetate | Not Detected [c] |
| Class 3 | isopropyl acetate | Not Detected [c] |
| Class 3 | methyl acetate | Not Detected [c] |
| Class 3 | 3-methyl-1-butanol | Not Detected [c] |
| Class 3 | methylethylketone | Not Detected [c] |
| Class 3 | methylisobutylketone | Not Detected [c] |
| Class 3 | 2-methyl-1-propanol | Not Detected [c] |
| Class 3 | pentane | Not Detected [c] |
| Class 3 | 1-pentanol | Not Detected [c] |
| Class 3 | 1-propanol | Not Detected [c] |
| Class 3 | 2-propanol | Not Detected [c] |
| Class 3 | propyl acetate | Not Detected [c] |

*The residual solvents (Class 1, Class 2 and Class 3) are based on *USP 467 Organic solvent residual*.
[a] The method detection limit was 2 ppm (1 μg/g = 1 ppm).
[b] The method detection limit was 5 ppm (1 μg/g = 1 ppm).
[c] The method detection limit was 10 ppm (1 μg/g = 1 ppm).

Results indicated a lack of solvent contaminants in the polymer developed in accordance with various embodiments disclosed herein.

Example 3: Biocompatibility of Polymer

In vitro and in vivo studies were conducted to assess the biocompatibility of the polymer designed in accordance with various embodiments disclosed herein. As will be shown in the following examples, the hydrogel is biocompatible (in the eye), and therefore suitable for ophthalmic usage.

i) In Vitro Study: Cell Viability Test on ARPE-19 Cells

Figure 8:
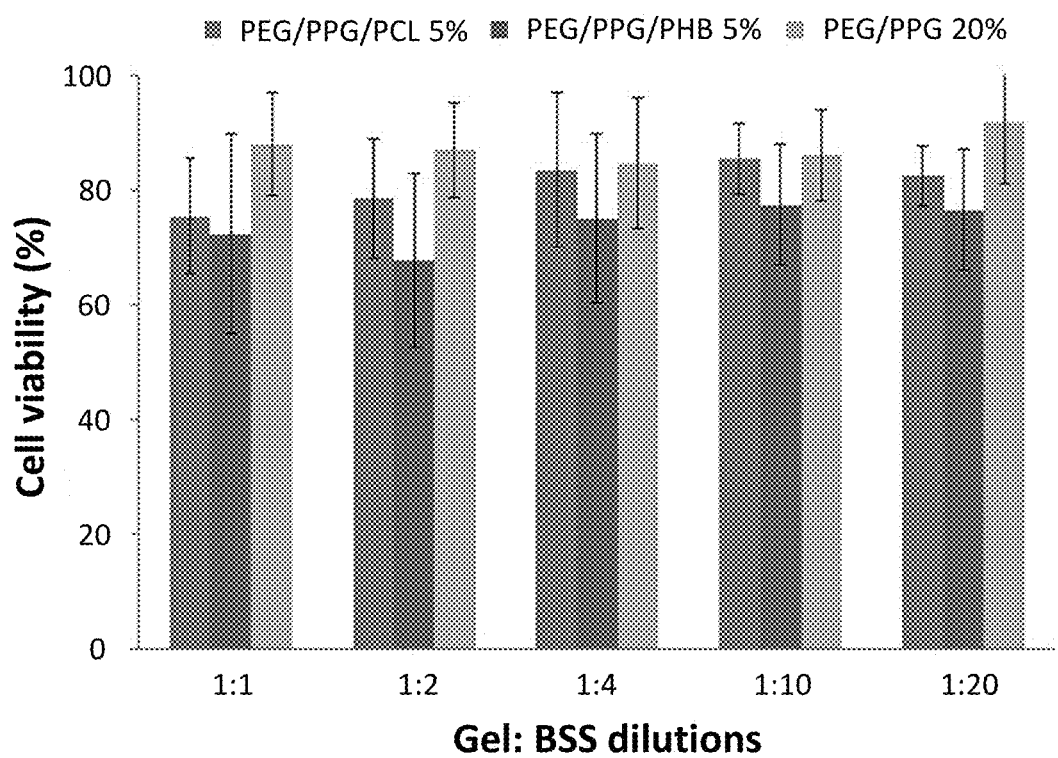
FIG. 8 is a graph showing the cell viability (%) of diluted gel solutions. Gel solutions used for the in vitro study are 5% (w/v) of PEG/PPG/PCL copolymer gel in water, 5% (w/v) of PEG/PPG/PHB copolymer gel in water and 20% (w/v) of PEG/PPG copolymer gel in water. The gel solutions were diluted with BSS solutions in the dilution ratio of 1:1, 1:2, 1:4, 1:10 and 1:20 respectively.

Diluted gel solutions were applied to confluent retinal pigment epithelium ARPE-19 cells (a human cell line) on 96-well plate and incubated for 24 h. Cell viability was performed by MTT assay. In brief, cultures are replaced with fresh medium before MTT assay. 10 μl MTT solution (5 mg/ml) was added to each well and incubated at 37° C. for 4 hours. After removal of MTT solution, 100 μl DMSO was added in each well to dissolve the formazan crystals. The plate was kept in dark for 10 minutes at room temperature before absorbance reading at 570 nm using a spectrophotometer. Gel solutions used for the in vitro study are (1) 5% (w/v) of PEG/PPG/PCL copolymer gel in water (2) 5% (w/v) of PEG/PPG/PHB copolymer gel in water and (3) 20% (w/v) of PEG/PPG copolymer gel in water. The gel solutions were diluted with BSS solutions in the dilution ratio of 1:1, 1:2, 1:4, 1:10 and 1:20 respectively. The results are shown in FIG. 8.

As shown, there is no difference of cell viability between gel groups. The mean ratios were 80.87±12.61% among all groups.

ii) In Vivo Study

For the in vivo study, 22 albino rabbits were used. Vitrectomy and (0.5-1.0 ml) thermogel was injected into the experimental eye. Vitrectomy and balanced salt solution (BSS) filled eyes served as controls. A 3 months follow-up in vivo study was conducted which include performing imaging such as slit-lamp, spectral-domain optical coherence tomography (SD-OCT), color fundus; and function test such as electroretinography (ERG) and intraocular pressure (IOP).

(a) Intraocular Pressure (IOP) Measurements

Figure 9:
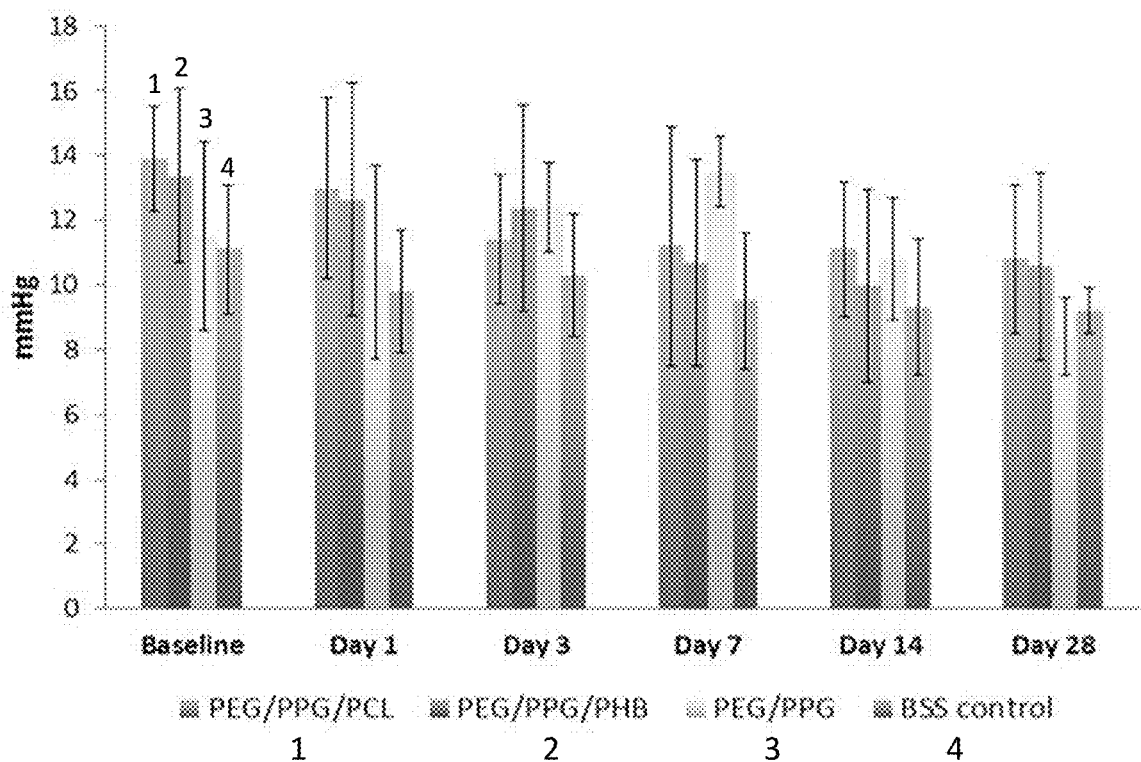
FIG. 9 is a graph showing the intraocular pressure (IOP) measurements obtained for thermogels namely, PEG/PPG/PCL copolymer (1), PEG/PPG/PHB copolymer (2) and PEG/PPG copolymer (3) over 28 days after surgery. BSS was used as the control (4).

Thermogels used for IOP measurements are (1) PEG/PPG/PCL copolymer (2) PEG/PPG/PHB copolymer and (3) PEG/PPG. BSS was used as the control. Measurements were taken over 28 days and the results are shown in FIG. 9.

As shown, IOP measurements remained in the normal range (between 8.4 and 13.9 mmHg). The mean value was 11.2±2.6 mmHg.

Figure 10:
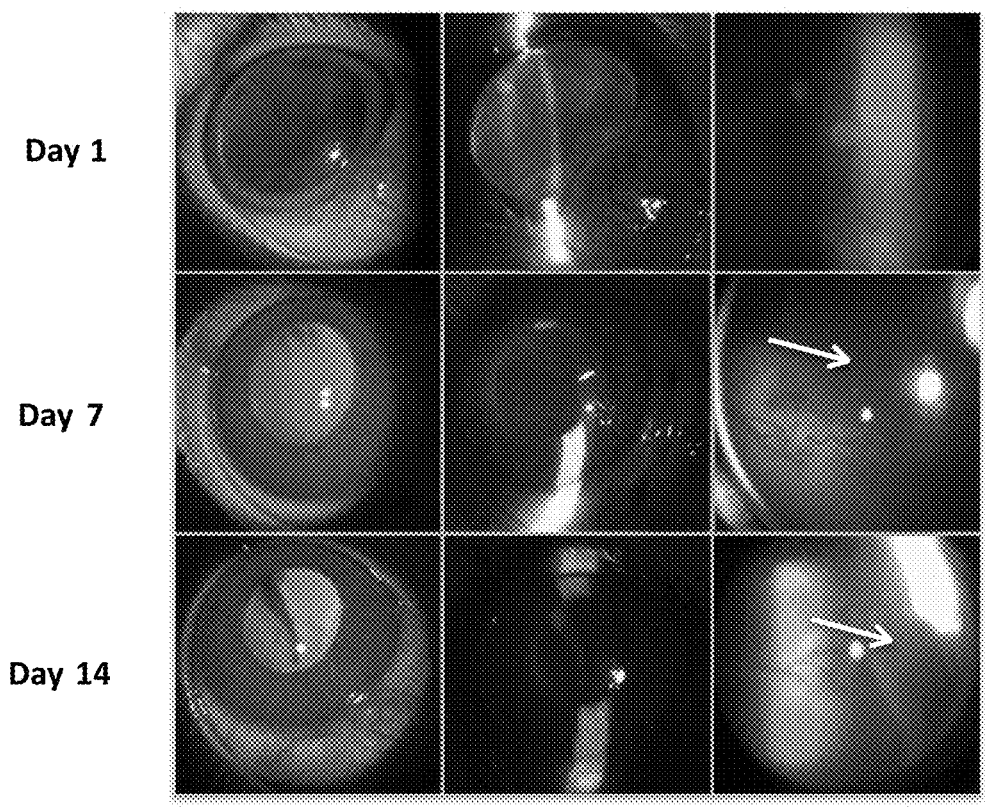
FIG. 10 shows images taken during slit lamp assessment on rabbit eyes injected with hydrogel without pH adjustment. Images were captured on day 1, day 7 and day 14 after surgery. The white arrows pointed retinal detachment on fundus image.

(b) Biocompatibility of Hydrogel without pH Adjustment:

Images taken during slit lamp assessment on rabbits are provided in FIG. 10. It is shown that retinal detachment occurred after one-week post surgery.

Post-Operation Day 1:
No evidence of inflammation.
Thermogel optically clear.
Fundus attached retina at POD1.

Post-Operation Day 7:
Retina was spontaneously detached (indicated by white arrow in FIG. 10).

Post-Operation Day 14:
Retinal detachment was enlarged (indicated by white arrow in FIG. 10).

(c) Biocompatibility of Hydrogel with pH Adjustment (pH 7.2-7.4)

SD-OCT at 1 Month after Surgery

Figure 11:
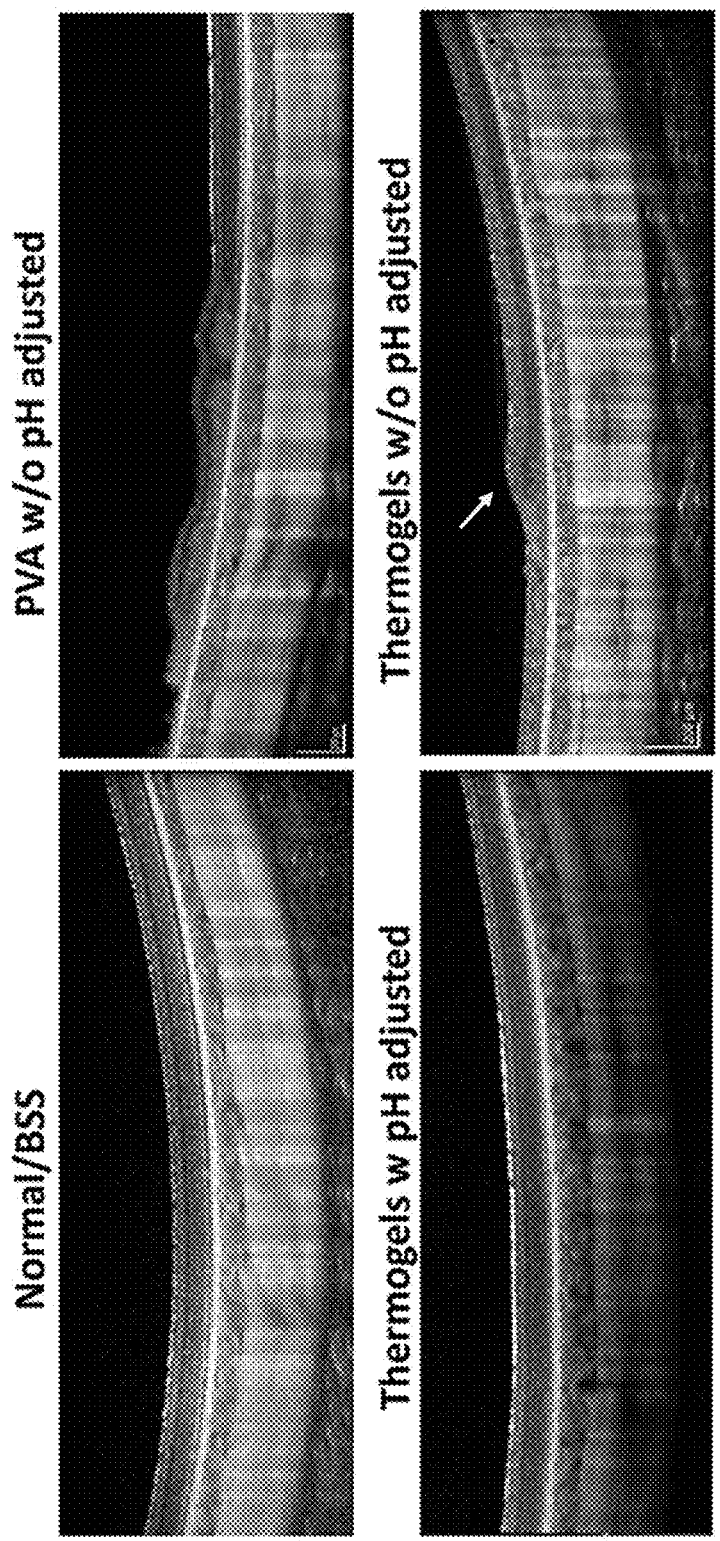
FIG. 11 shows spectral-domain optical coherence tomography (SD-OCT) images of rabbit eyes injected with normal BSS, PVA without pH adjustment, thermogels with pH adjustment and thermogels without pH adjustment (white arrow indicates area of retinal necrosis). The images were captured 1 month after surgery.
Figure 12:
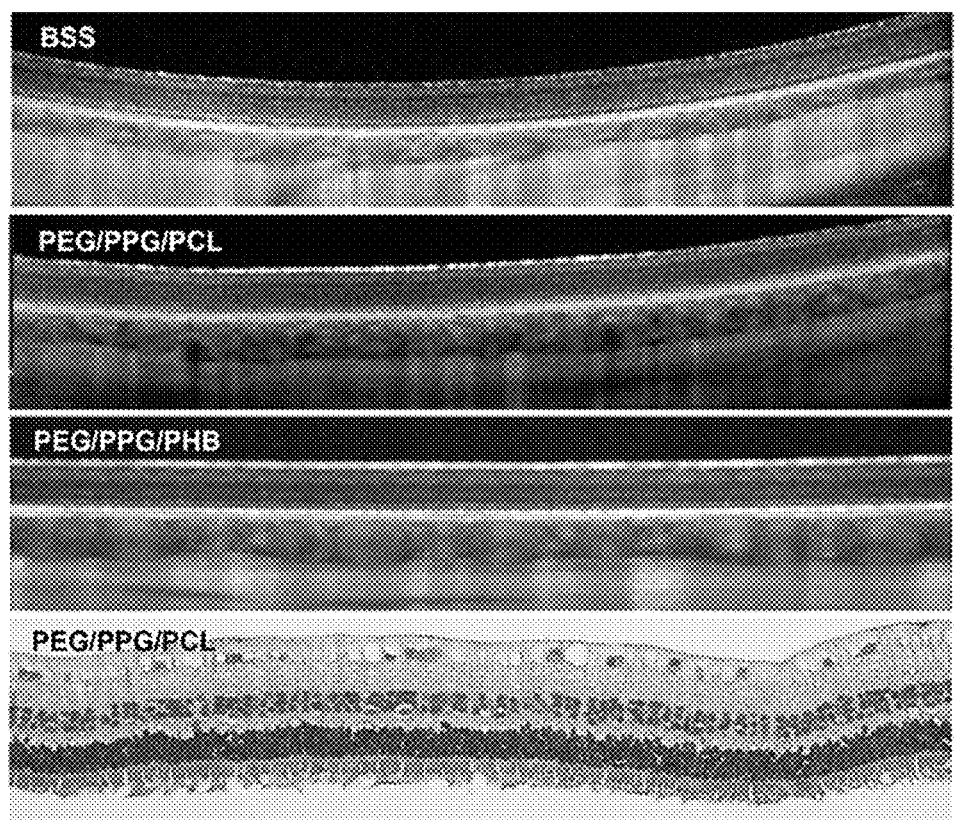
FIG. 12 shows spectral-domain optical coherence tomography (SD-OCT) images and histology of rabbit eyes injected with normal BSS, PEG/PPG/PCL copolymer, PEG/PPG/PHB copolymer.

Spectral-domain optical coherence tomography (SD-OCT) images of rabbit eyes taken 1 month after surgery are provided in FIG. 11. SD-OCT images and histology are provided in FIG. 12.

SD-OCT images showed normal reflection bands referring to retinal layers among BSS control and thermogel filled eyes. Normal retinal structure was presented on histology after haemotoxylin and eosin staining (H&E staining).

Scotopic Electroretinography (ERG)

Figure 13:
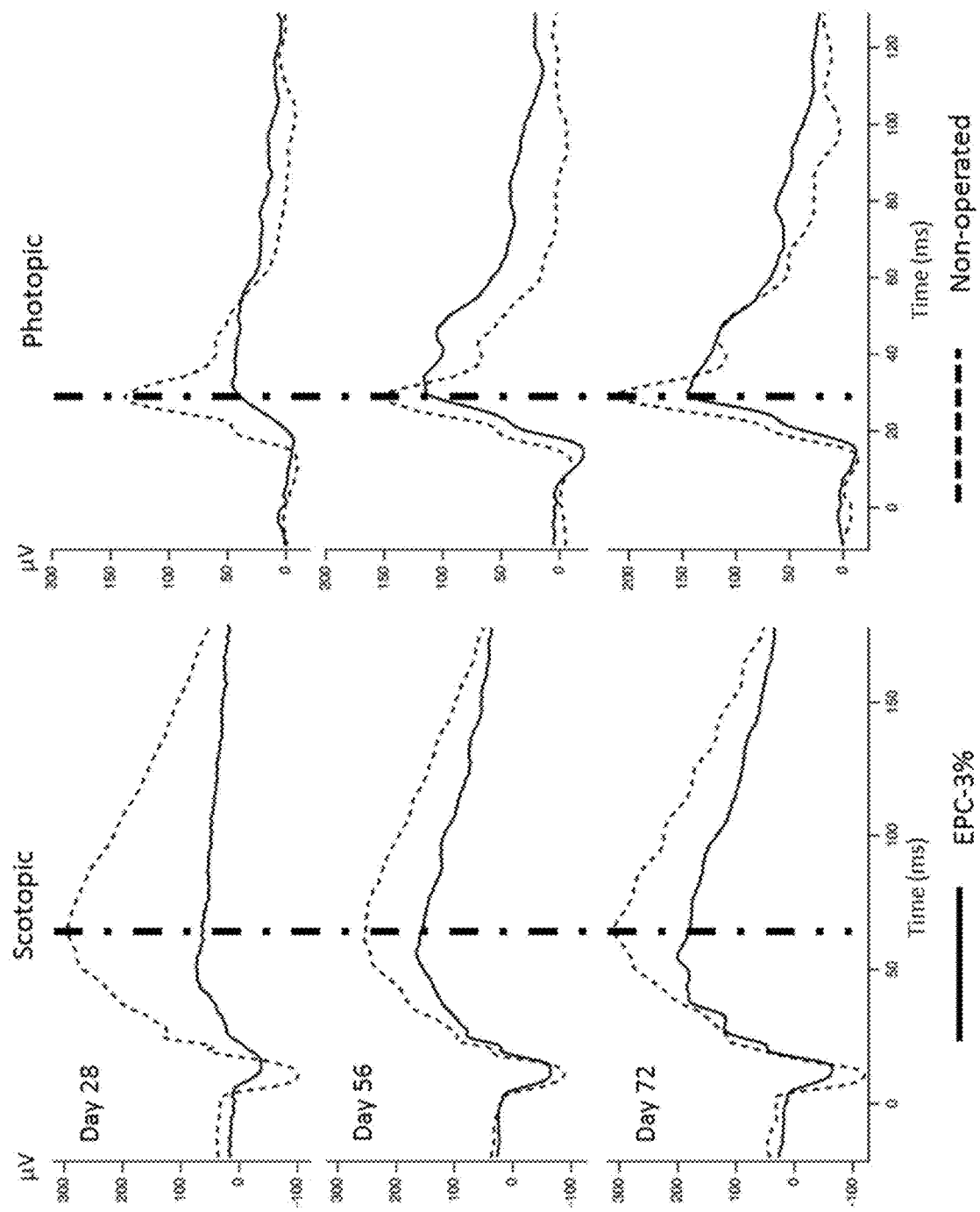
FIG. 13 shows scotopic and photopic electroretinograms of rabbit eyes injected with PEG/PPG/PCL copolymer, alongside together with a non-operated control. The electroretinograms were recorded on day 28, day 56 and day 72 after surgery.

Scotopic electroretinograms of rabbit eyes are provided in FIG. 13. Decreased b waves were observed on electroretinography (ERG) post surgery, which was slowly recovering till 3 months. Scotopic and photopic ERG waveforms in rabbits at 3 months post-vitrectomy, and replacement with thermogel, showed both normal retinal structure and retinal function.

Example 4: Demonstration of Biocompatibility of EPC Thermogels

Figure 14:
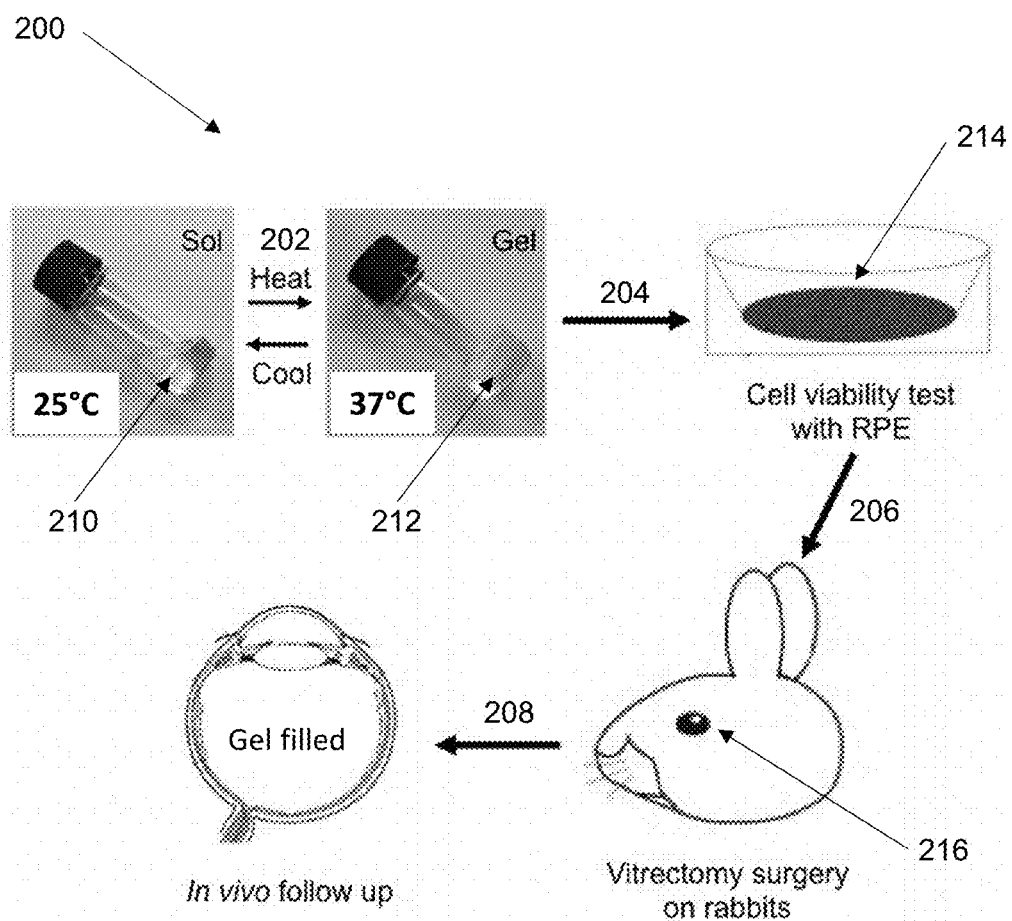
FIG. 14 is a schematic flowchart 200 for illustrating the experiment set-up for demonstrating biocompatibility/non-toxicity of the polymer designed in accordance with various embodiments disclosed herein.

FIG. 14 is a schematic flowchart 200 for illustrating the experiment set-up for demonstrating biocompatibility/non-toxicity of the polymer designed in accordance with various embodiments disclosed herein. At step 202, a sol-gel transition occurs upon a change in temperature from 25° C. to 37° C. The polymer in the sol state 210 rapidly forms a thermogel 212 at 37° C., which may transit back to its original state 210 upon cooling to 25° C. At step 204, thermogel 212 is applied to retinal pigment epithelium (RPE) cells and cell viability test is performed on said cells 214. At step 206, thermogel 212 is injected into rabbit eye 216 during vitrectomy surgery. At step 208, the rabbit eye is followed up post-operatively for at least up to 6 months.

EPC Thermogels

In the following examples 4, 5 and 6, the developed copolymer thermogel consists of hydrophilic PEG, thermosensitive poly(propylene glycol) (PPG) and hydrophobic, biodegradable poly(ε-caprolactone) (PCL) segments linked together via urethane bonds (herein termed "EPC"). The ratio of PEG:PPG is 4:1 and the concentration of PCL is 1 wt % of the EPC polymer.

Rheological Characterisation of EPC Thermogels

The sol-gel transition properties of different concentrations of thermogels (3 wt %, 7 wt %, 12 wt %) were characterized by rheological analysis.

Figure 15A:
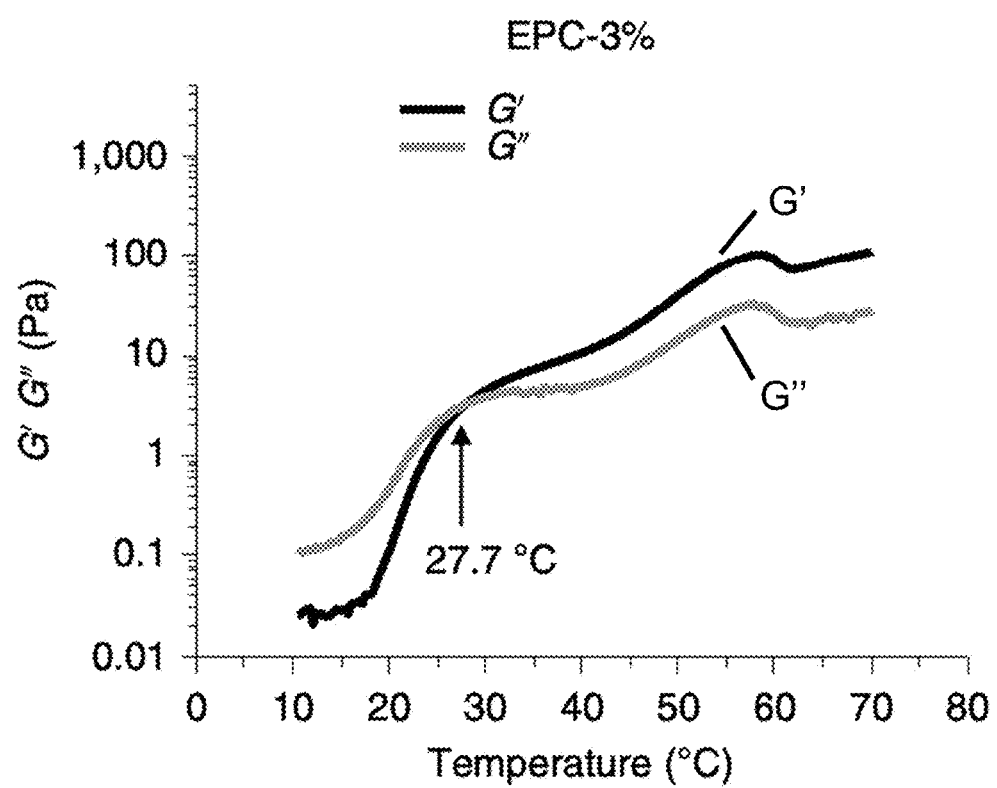
FIGS. 15A, 15B and 15C are graphs showing the temperature ramp of EPC thermogelling solutions with concentration range from 3 to 12 wt %, measured at strain=1%, frequency=1 Hz and temperature ramp rate=3° C./min. In the thermogelling aqueous solutions, the ratio of PEG:PPG is 4:1 and the concentration of PCL is 1 wt % of the polymer. The crossover point of G' and G" is the point when sol-gel transition occurred.
Figure 15B:
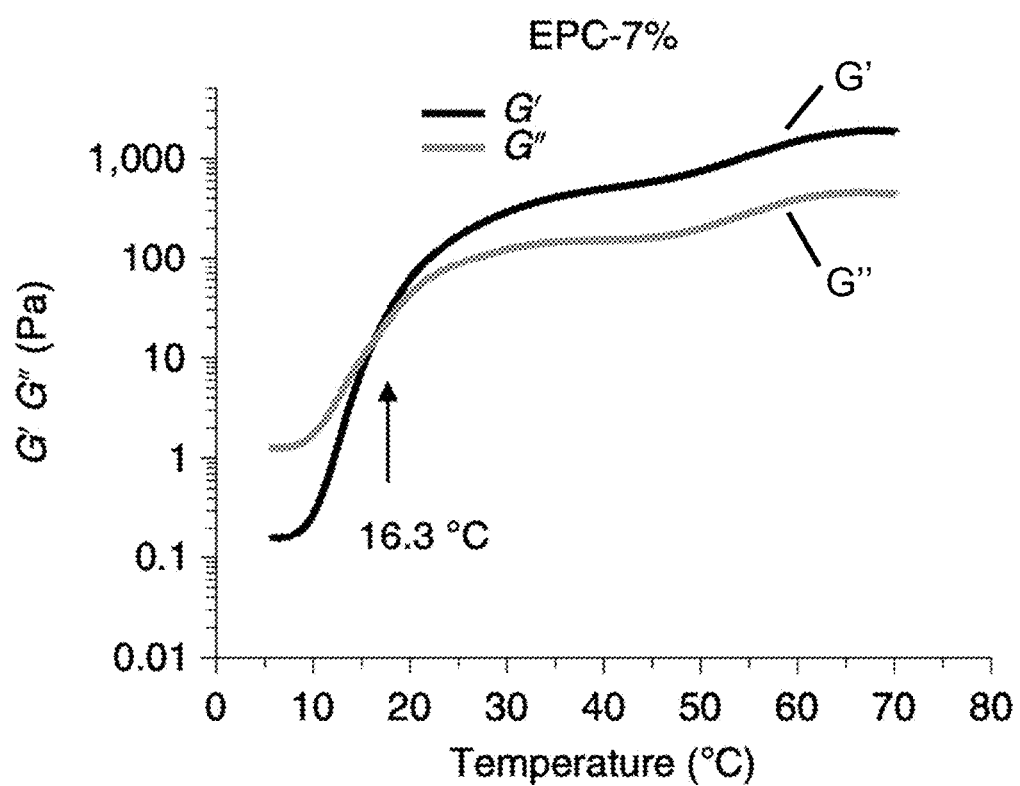
Figure 15C:
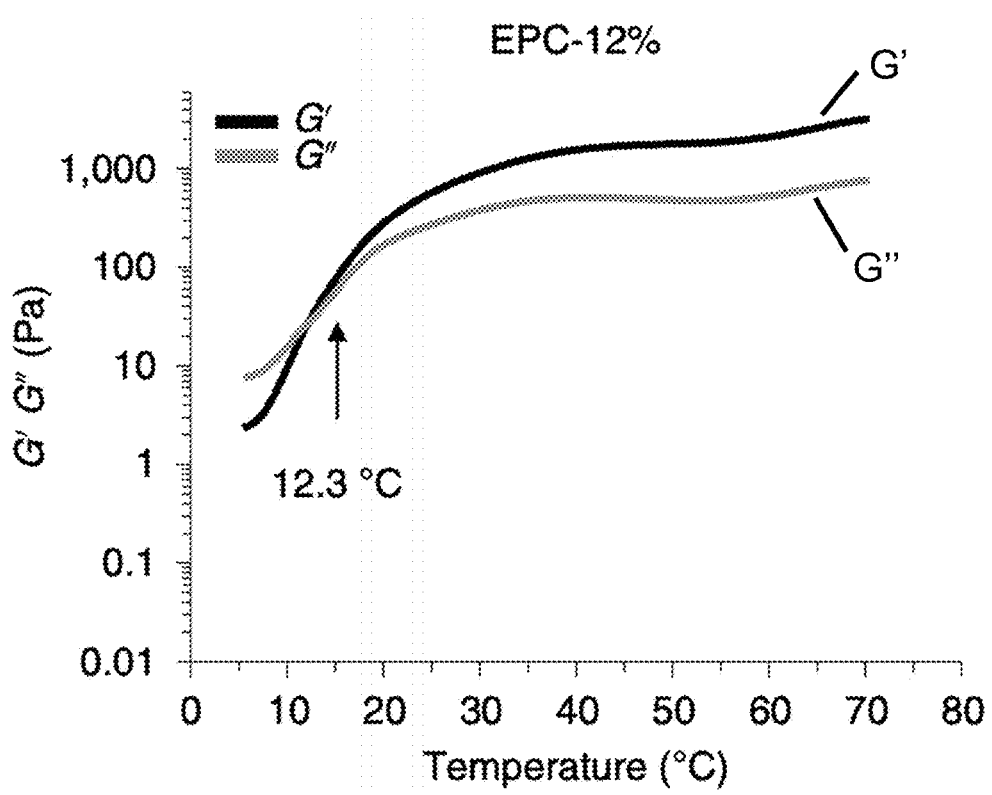

The storage and loss moduli (G' and G") were determined from 10° C. to 70° C., as shown in FIG. 15A to 15C. The gelation temperature decreases from 27.7° C. to 12.3° C., over a range of 3 to 12 wt % EPC concentrations.

Figure 15D:
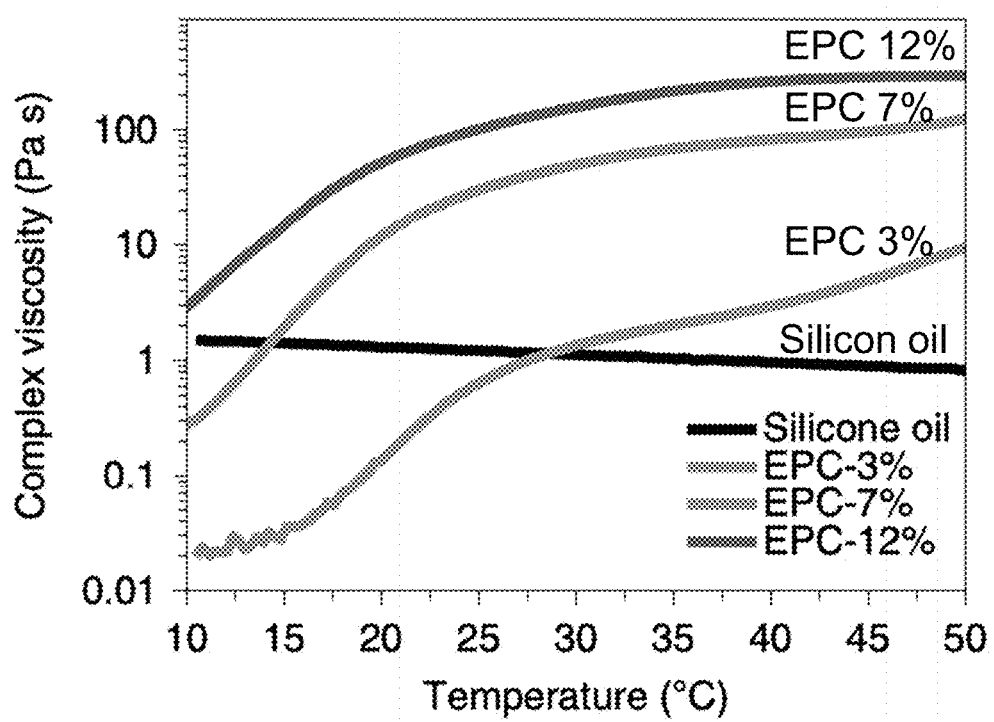
FIG. 15D is a graph showing the complex viscosity of solutions determined in an oscillation temperature sweep experiment. The y-axis is put in log scale for clarity. Commercial available silicone (Oxane® 1300, Bausch & Lomb, USA) oil was used as a control.

Complex viscosity of solutions were determined in an oscillation temperature sweep experiment (FIG. 15D). At gel state, the EPC thermogels exhibit a complex viscosity higher than that of silicone oil.

Figure 15E:
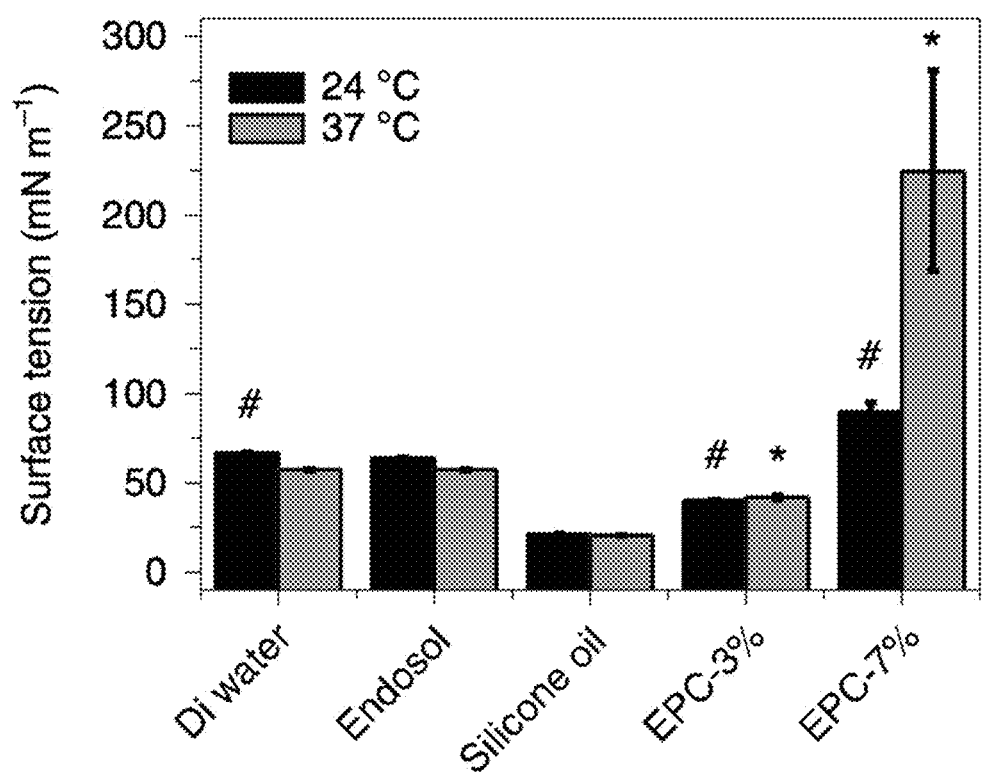
FIG. 15E is a graph showing the surface tension of solutions conducted with tensiometer using a DuNouy ring at specific temperature.

Surface tension of solutions were conducted with tensiometer using a DuNouy ring at specific temperature (FIG. 15E). EPC-12% was too viscous for the test. Data represents mean±SD of 10-30 data points. Statistical analysis was performed using Student's t-test: # $p<0.05$ compared to Endosol buffer at 24° C. *$p<0.05$ compared to Endosol buffer at 37° C.

Figure 15F:
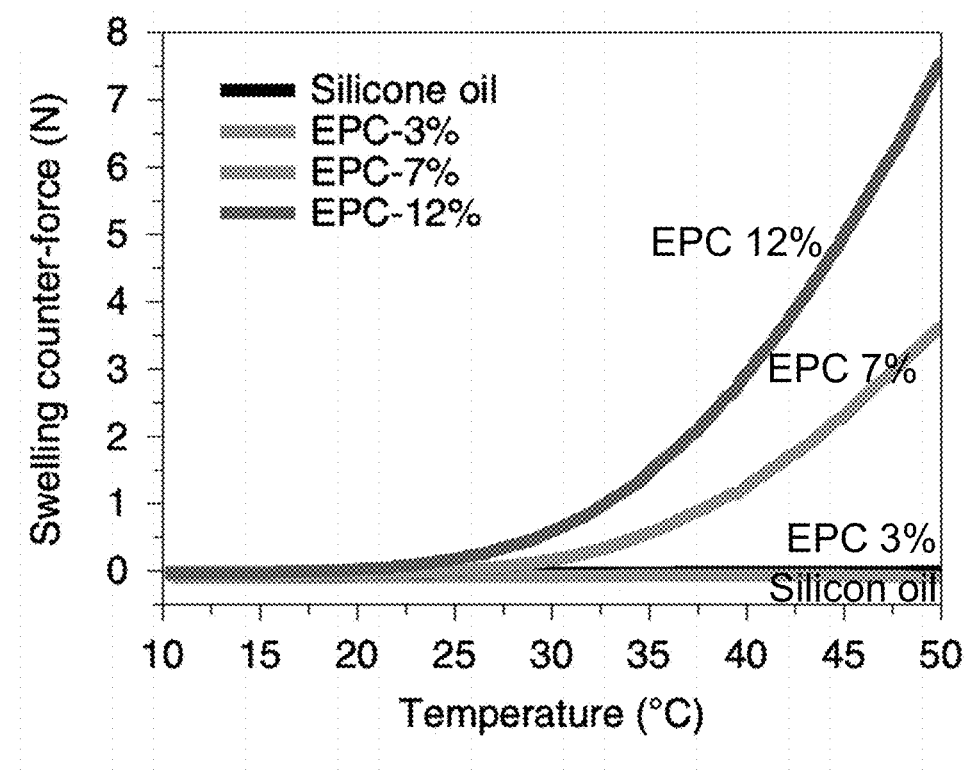
FIG. 15F is a graph showing the swelling counter force (N) of solutions as determined from sweep experiments displayed over temperature from 10 to 50° C.

Swelling counter force (N) of solutions as determined from sweep experiments were displayed over temperature from 10 to 50° C. (FIG. 15F). Swelling counter force generally increases with temperature, with EPC 12% (2.031 N)>EPC 7% (0.843 N)>EPC 3% (−0.066 N), silicon oil (−0.023 N) at 37° C.

Figure 16:
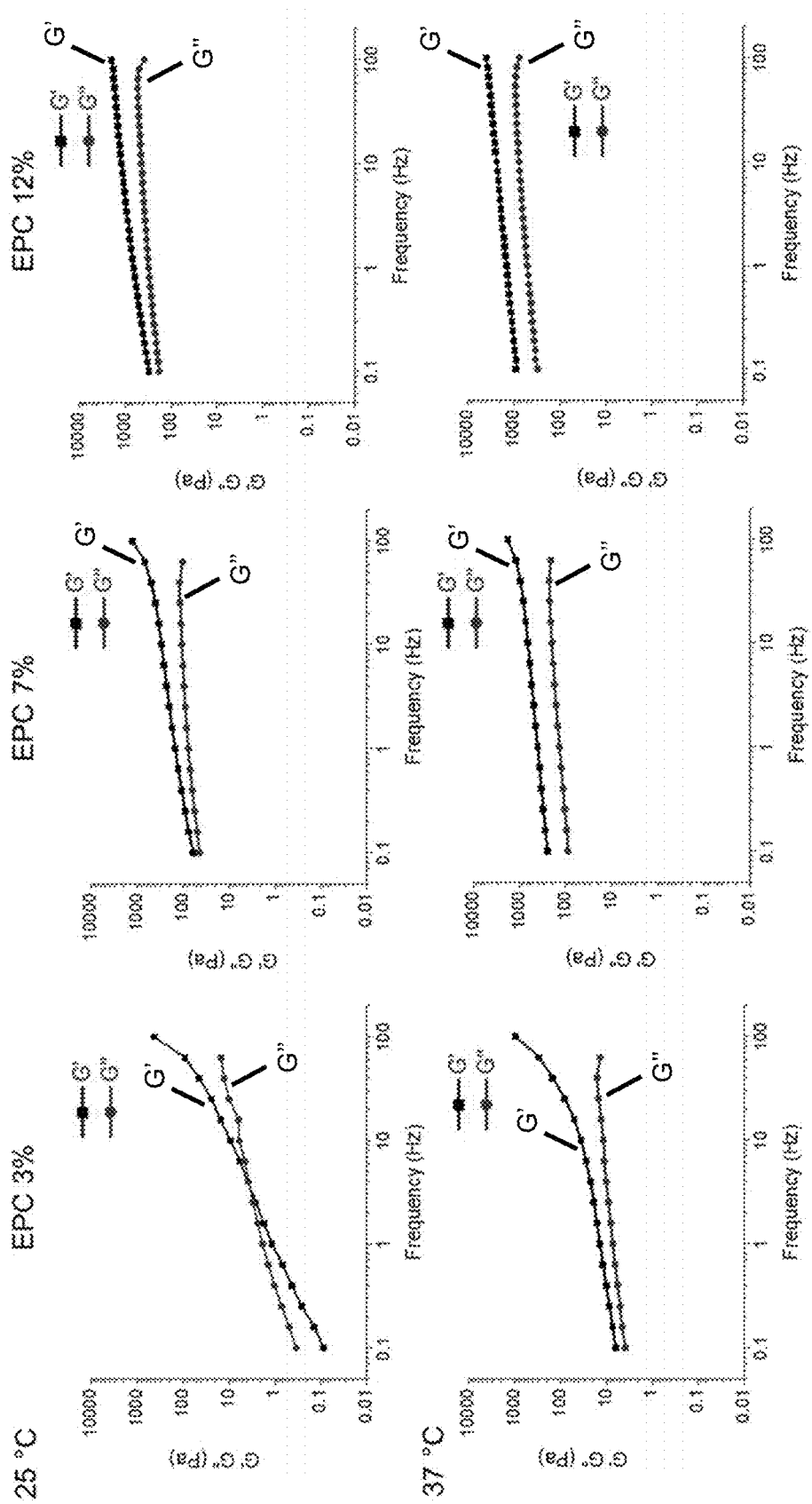
FIG. 16 shows strain amplitude sweep of thermogelling solutions with concentrations of 3 wt. %, 7 wt. % and 12 wt. %, from 0.1 to 100% strain, at both and 37° C. respectively.
Figure 17:
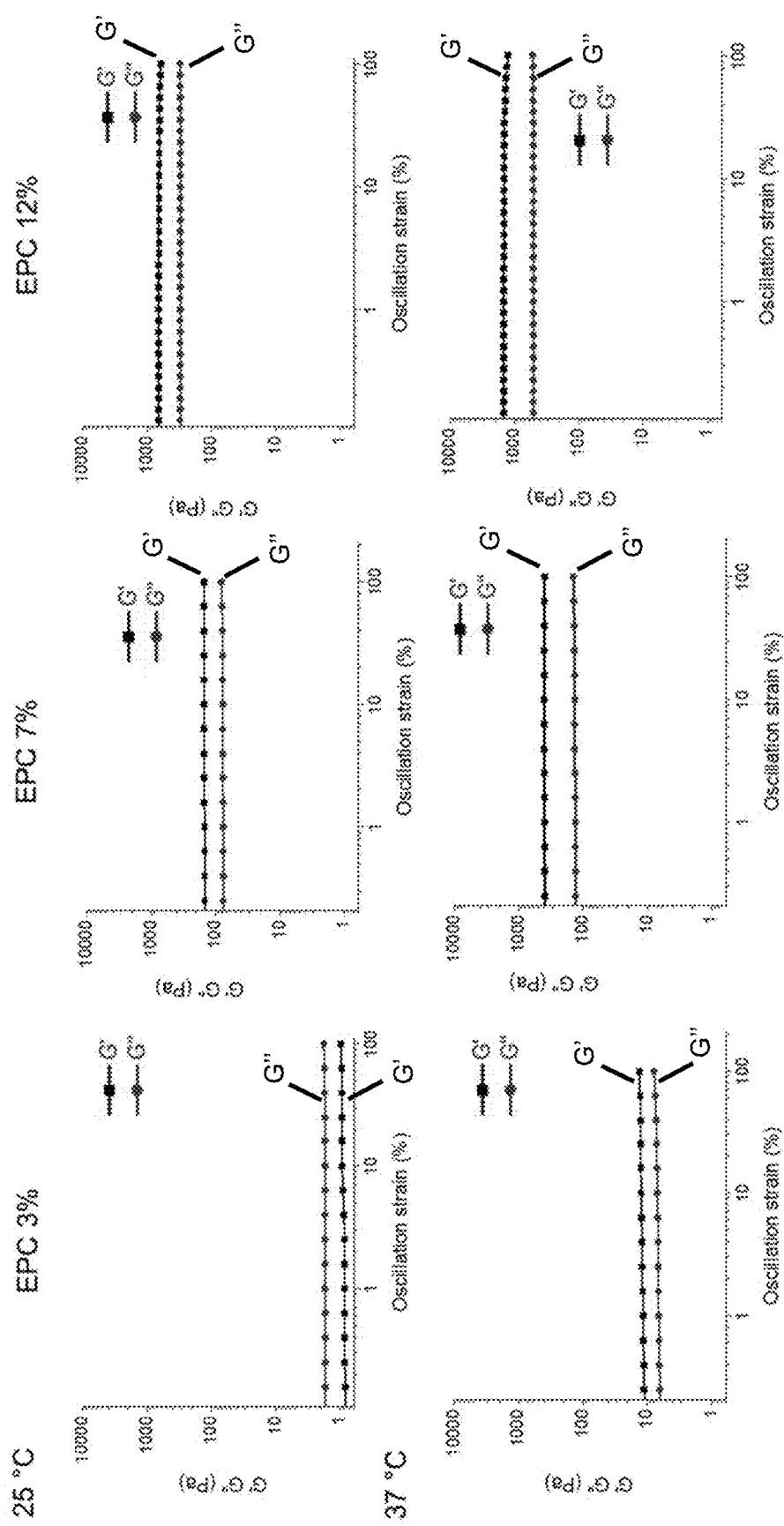
FIG. 17 shows frequency sweep of thermogelling solutions with concentrations of 3 wt. %, 7 wt. % and 12 wt. %, from 0.1 to 100 Hz, at both 25 and 37° C. respectively.

Oscillation frequency sweep and oscillation amplitude sweep experiments were also performed (FIG. 16 and FIG. 17). FIG. 16 shows strain amplitude sweep of thermogelling solutions with concentrations of 3 wt. %, 7 wt. % and 12 wt. %, from 0.1 to 100% strain, at both 25 and 37° C. respectively. FIG. 17 shows frequency sweep of thermogelling solutions with concentrations of 3 wt. %, 7 wt. % and 12 wt. %, from 0.1 to 100 Hz, at both 25 and 37° C. respectively.

In Vivo Biocompatibility of EPC Thermogels

In vivo biocompatibility of EPC thermogels was demonstrated using ophthalmic surgical models in New Zealand White (NZW) rabbits. 23 gauge core-vitrectomy were performed in NZW rabbits and 25 eyes were injected with sol-state EPC thermogel. All EPC thermogels were observed to form a gel in-situ within the vitreous during vitreo-retinal surgery. These rabbits were followed up post-operatively for up to 6 months for potential complications.

In the eyes filled with gel, on examination, there was clear cornea and lens, with normal retinal appearance and normal intra-ocular pressure (IOP). In addition, normal retinal architecture was preserved on haematoxylin and eosin (H&E) stain.

Figure 18:
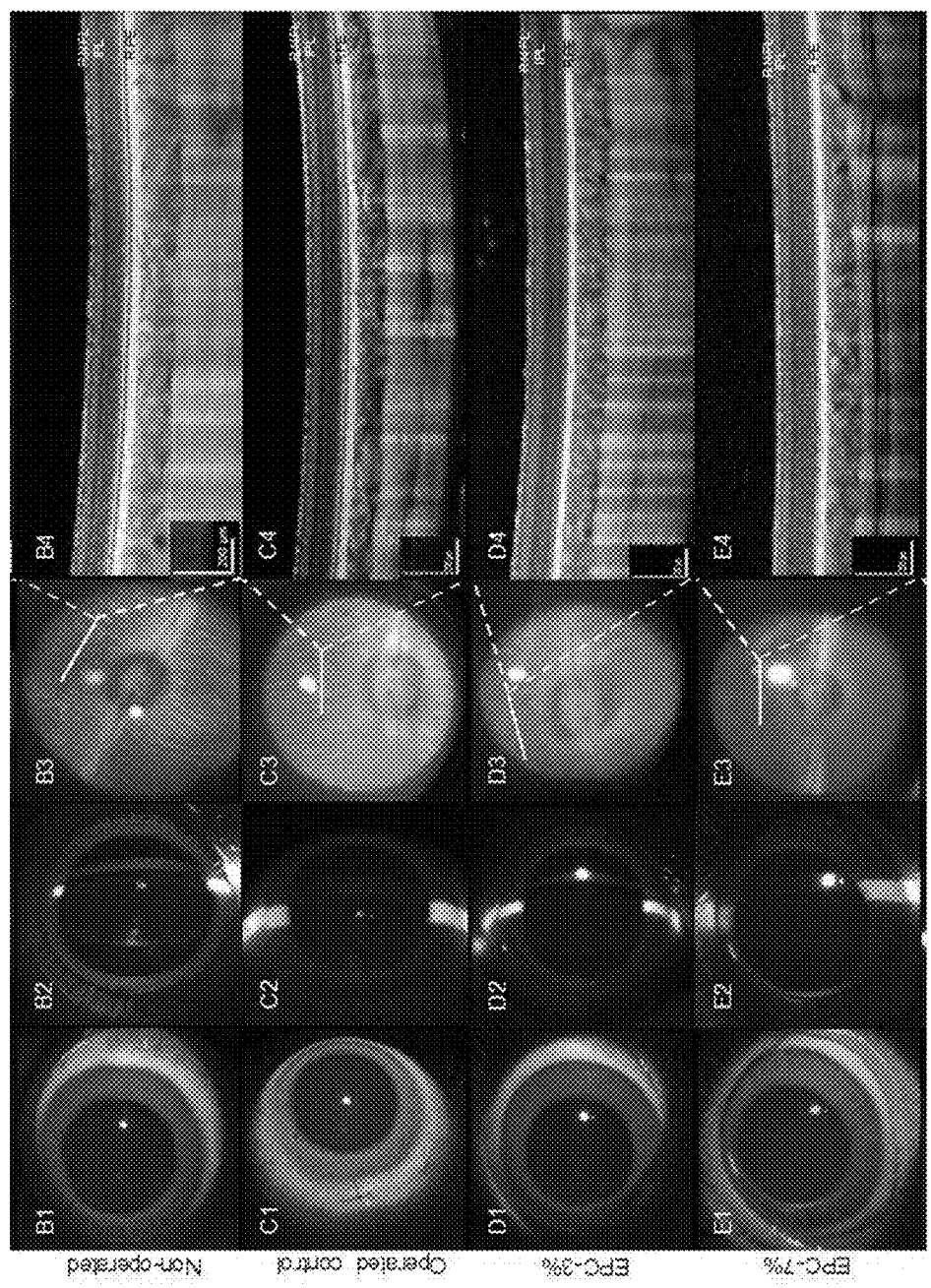
FIG. 18 shows spectral-domain optical coherence tomography (SD-OCT) images captured during live in vivo imaging of rabbits implanted with different hydrogels at Day 7 post-operation. Scale bars represent 200 µm in B4, C4, D4 and E4.

FIG. 18 shows live in vivo imaging of rabbits implanted with different hydrogels at Day 7 post-operation. Slit lamp pictures show negligible inflammation in the anterior chamber (see column B1 to E1), absence of cataract formation (see column B2 to E2), and optically clear hydrogel in the vitreous cavity. The optic disc and retinal vascular architecture appear normal (see column B3 to E3). The white lines indicate the position at which SD-OCT images were taken (1-2 optic disc distance superior to the disc). Rabbits implanted with all three concentrations (3 wt %, 7 wt % and 12 wt %) of EPC hydrogels have normal retinal architecture as observed in SD-OCT images (see column D4, E4).

Figure 19:
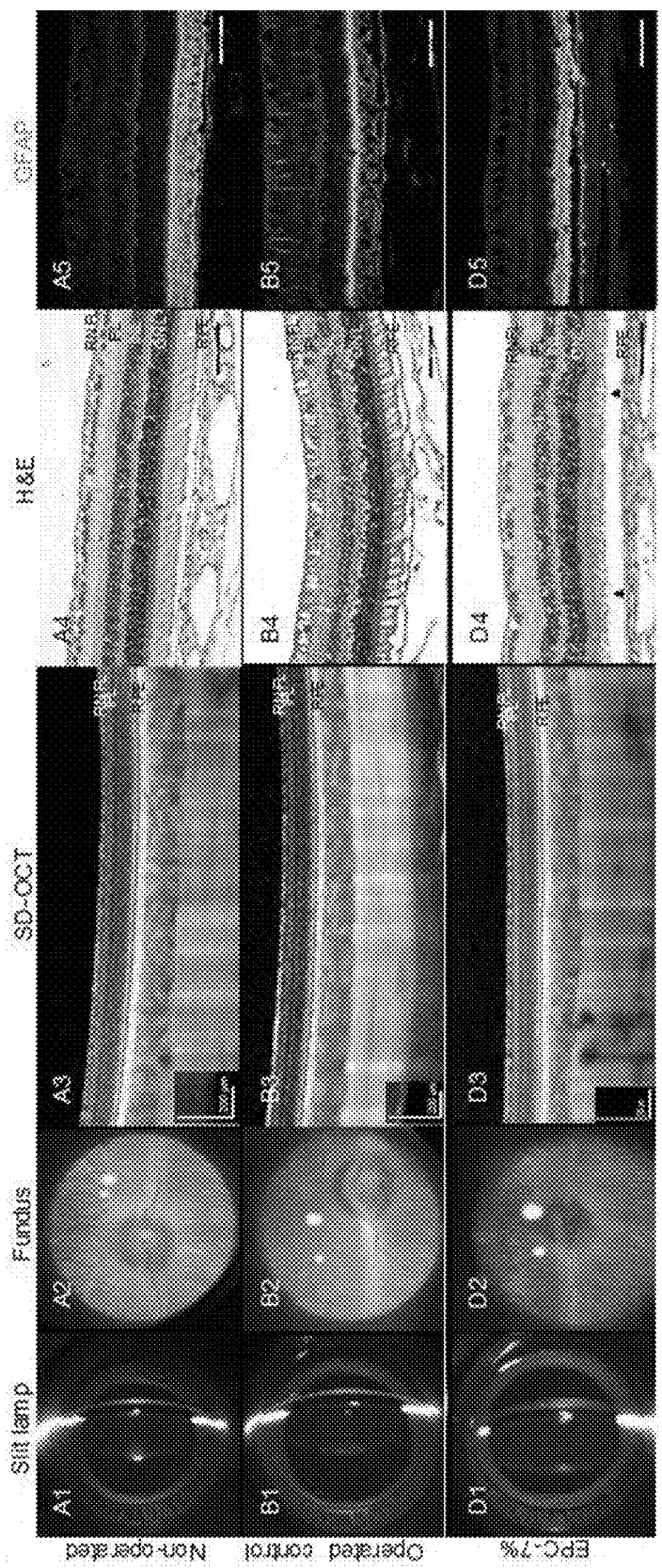
FIG. 19 shows in vivo imaging and ex vivo retinal analysis of rabbits at 3-months post-implantation of the EPC gels. Scale bars represent 200 µm in A3, B3, D3. Scale bars represent 50 µm in A4, B4, D4, A5, B5 and D5.

FIG. 19 shows in vivo imaging and ex vivo retinal analysis of rabbits at 3-months post-implantation of the EPC gels. In the 1$^{st}$ column (A1, B1 and D1), the slit lamp images of non-operated rabbits, operated BSS controls and EPC 7% thermogels showed no significant inflammation and cataract formation. In the 2$^{nd}$ column (A2, B2 and D2), fundus images revealed normal optic disc appearance and vessel morphology in all groups. In the 3$^{rd}$ column (A3, B3 and D3), normal optical coherence tomography (OCT) images were obtained in all three groups. Haematoxylin and eosin (H&E) histology analysis was performed in all 3 groups which was normal, as shown in 4$^{th}$ column (A4, B4 and D4).

Figure 20:
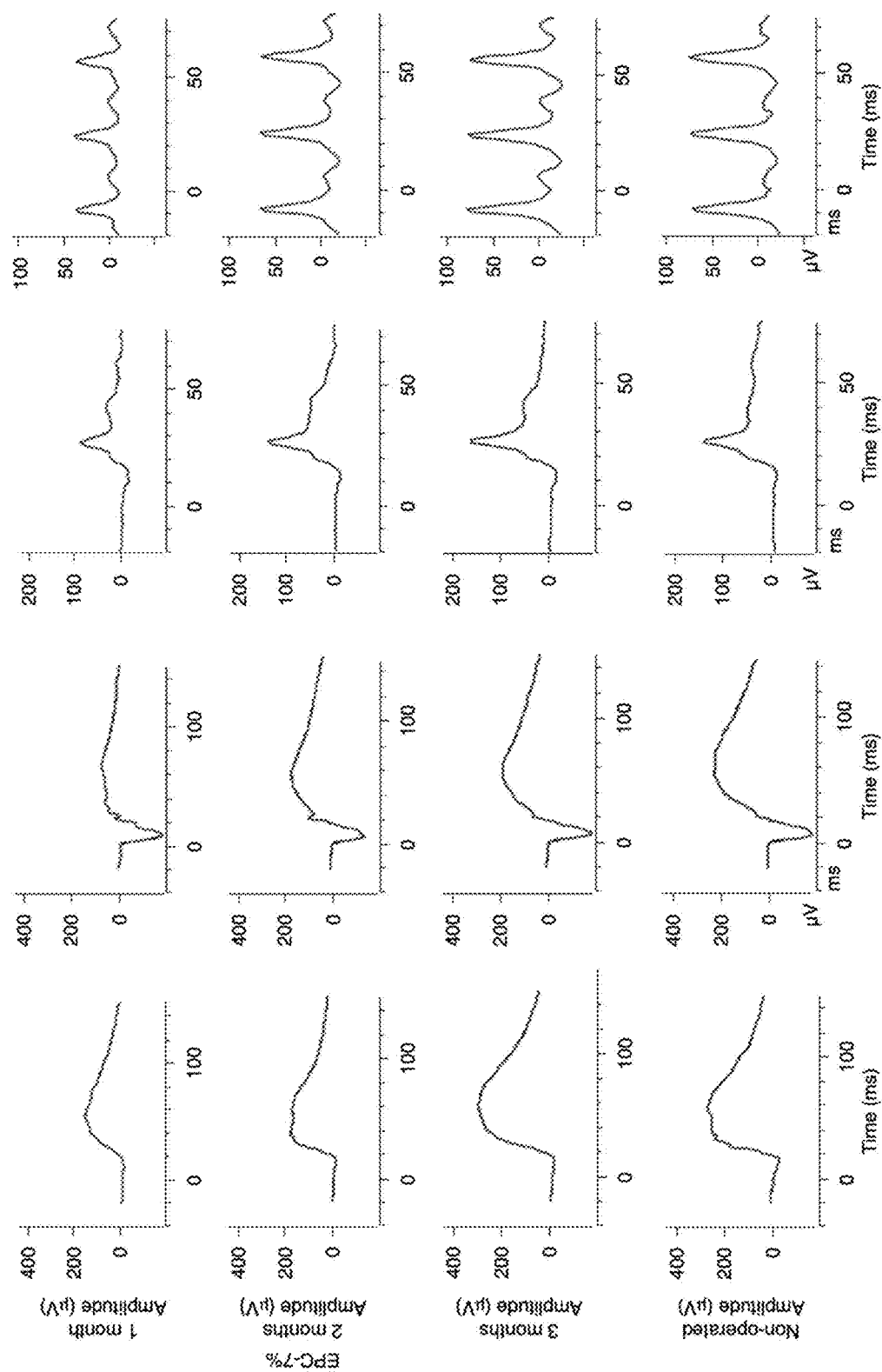
FIG. 20 shows the functional assessment of rabbit retina by electroretinography (ERG). Rabbit eyes were implanted with EPC 7 wt % and monitored over 1 month (herein termed "1M"), 2 months (herein termed "2M") and 3 months (herein termed "3M").

In vivo functional assessment of the retina was performed by electro-retinography (ERG), which shows mild loss of scotopic b-wave and photopic 30 Hz flicker response at 1 month with complete recovery by 3 months, that was maintained at 6 months (FIG. 20). In rabbit eyes implanted with EPC-7% gel, at 1 month, there was only a mild loss of scotopic b wave-amplitude and 30 Hz flicker ERG amplitudes, but complete recovery by 3 months compared to normal.

Example 5: Confirmation of Suitability and Efficacy as Tamponade Agent

The suitability and efficacy as an internal tamponade agent was confirmed in a surgical non-human primate (NHP) retinal detachment model.

Briefly, retinal detachment was induced in 2 NHPs, followed by retinal detachment repair and full-fill injection gel into the vitreous cavity (approximate 1.5 to 2.0 ml).

Figure 21:
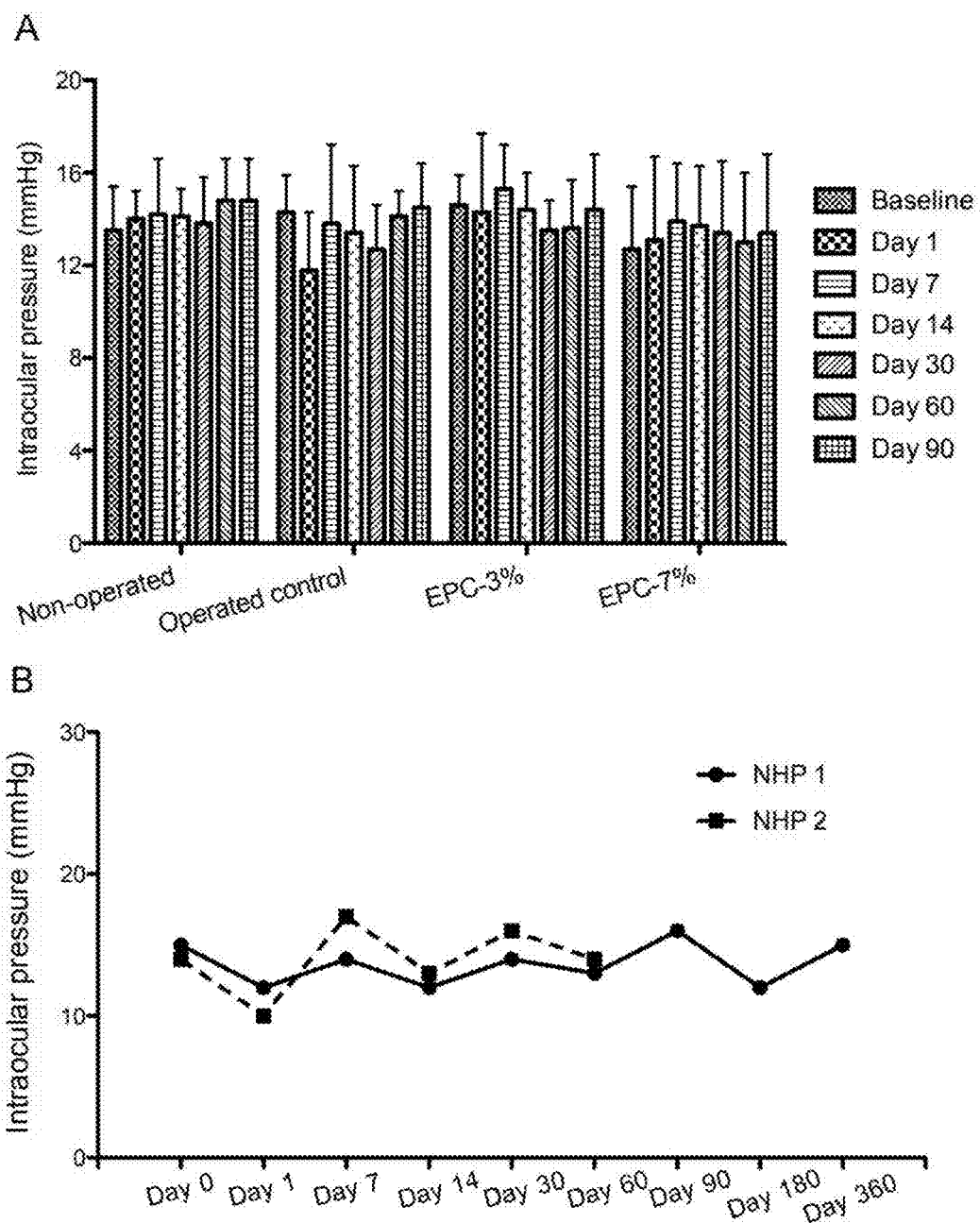
FIG. 21 shows the intraocular pressure (IOP) after implantation of EPC thermogels. (A) IOP follow up in rabbits. Data are plotted as the mean±s. e. m in all groups. (B) IOP follow up in two NHPs.

The intraocular pressure (IOP) after implantation of EPC thermogels is provided in FIG. 21. FIG. 21A shows the IOP follow up in rabbits. The mean IOP among non-operated rabbit eyes is 14.3±1.8 mmHg (range from 10.6 to 16.4 mmHg). The mean IOP in rabbits implanted with 3% and 7% EPC thermogel is within normal limits (13.5±2.6 mmHg, range from 7.6 to 18 mmHg). FIG. 21B shows the IOP follow up in two NHPs. IOP in both EPC-7% implanted eyes were maintained within normal limits (range from 12 to 17 mmHg).

Figure 22A:
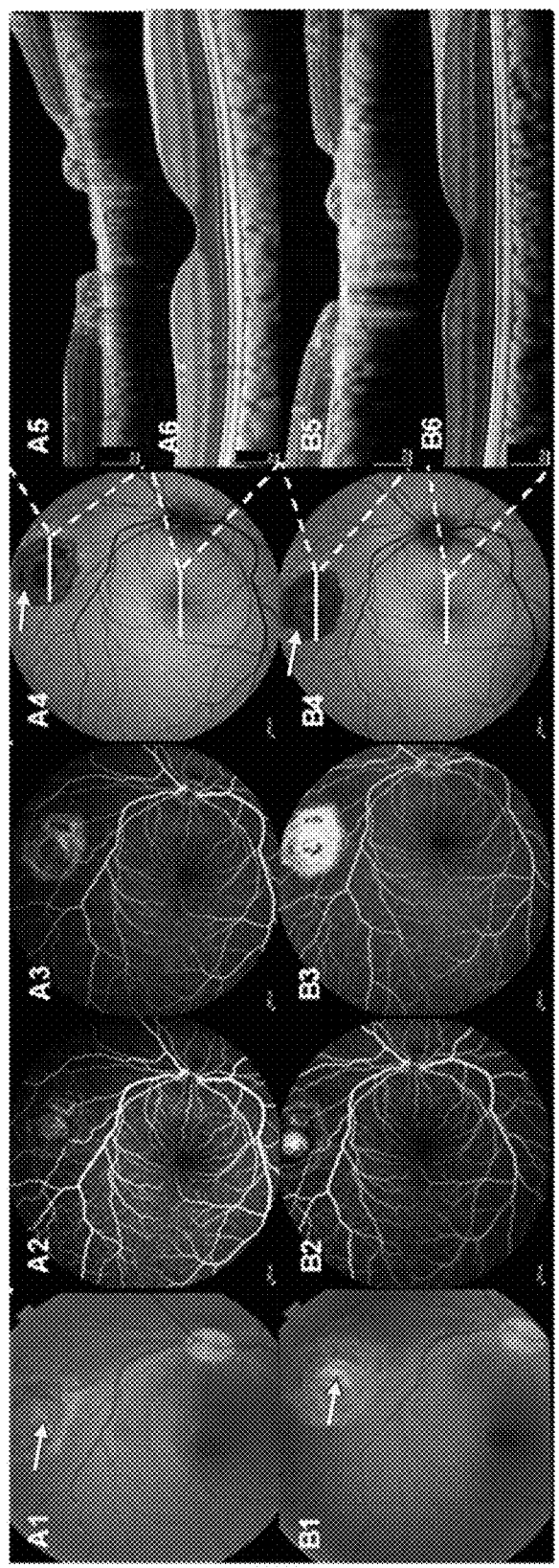
FIG. 22A shows ophthalmic images taken post-retinal detachment surgery. Images A1 to A6 were taken at 3-months post-retinal detachment surgery. Images B1 to B6 were taken at 12-months post-retinal detachment surgery.
Figure 22B:
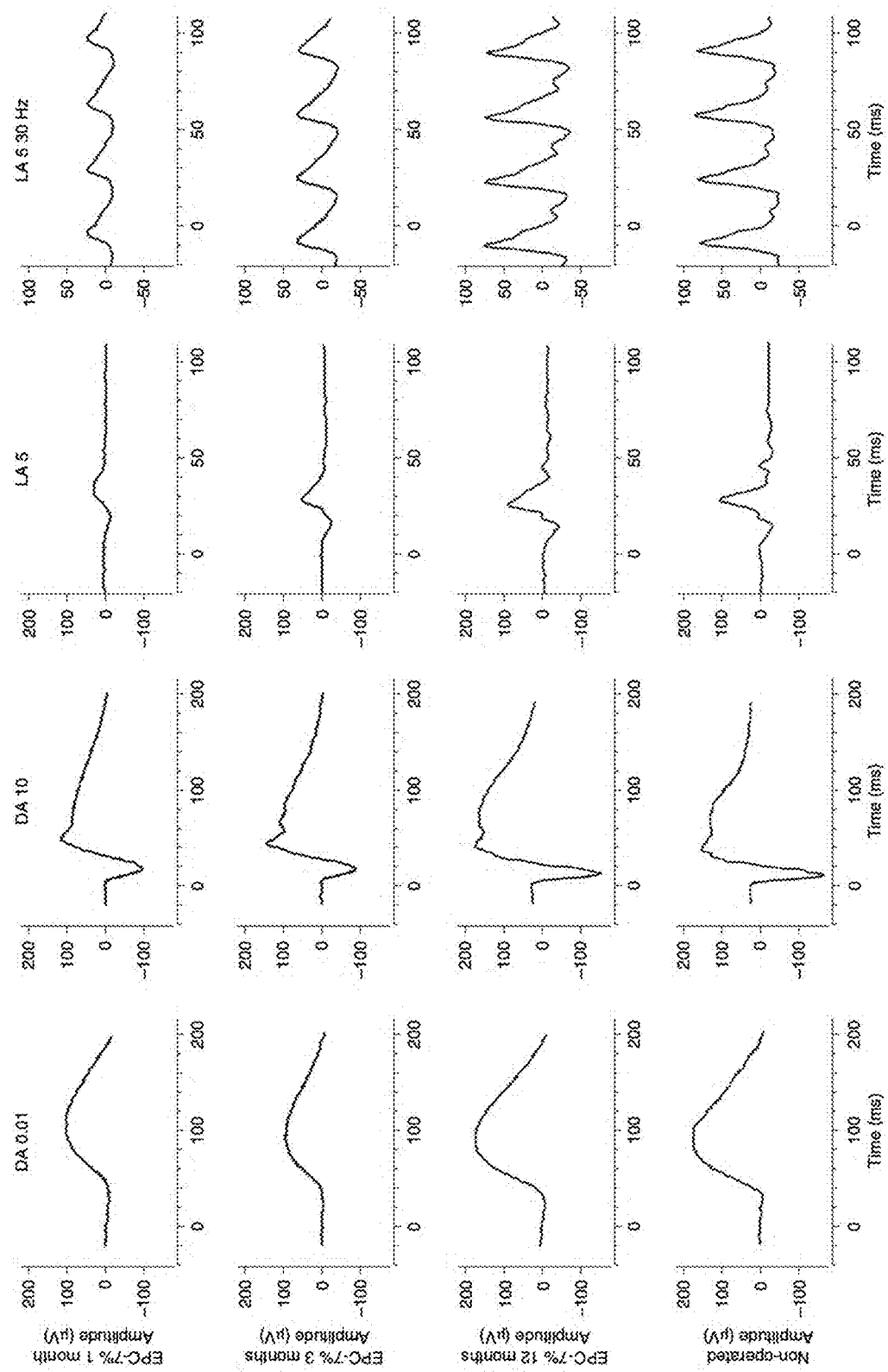
FIG. 22B shows pattern ERG of EPC-7% gel filled eye.

A non-human primate (NHP) surgical retinal detachment model demonstrated EPC-7% thermogel to be an effective endotamponade. Ophthalmic images were taken at 3-months (see images A1 to A6) and 12-months (see images B1 to B6) post-retinal detachment surgery, as shown in FIG. 22A. Color fundus images of EPC-7% filled eye showed clear vitreous, attached retina and formation of chorio-retinal adhesion around the iatrogenic retinal tear (indicated by white arrows, in A1 and B1). Fluorescein angiography images show normal retinal vasculature without any leakage (A2 and B2 were taken within 30 seconds after fluorescein injection, while A3 and B3 were taken 10 minutes later). Auto-fluorescence images (imaging the auto-fluorescence of lipofuscin to blue laser light at the level of the retinal pigment epithelium (RPE) using a SLO) showed normal retina surrounding the lasered area of retinal tear (indicated by white arrows, in A4 and B4). The SD-OCT scan obtained at the site of the retinal tear (indicated by white line in A4 and B4) demonstrated sufficient chorioretinal adhesion, and with surrounding flat (re-attached) retina at both 3 months (A5) and 12 months (B5). SD-OCT scan of the macula (indicated by white line in A4 and B4) showed both normal foveal contour and retinal architecture at 3 months (A6) and 12 months (B6). Full field ERG showed mild cone more than rod dysfunction at 1-month post-surgery, with substantial recovery at 3 months and full recovery by 12 months. In FIG. 22B, pattern ERG showed normal waveform in EPC-7% gel filled eye compared to baseline at 12 months, consistent with normal macular function. In FIG. 22C, H&E analysis of the macular of EPC-7% filled eye (FIG. 22D) is normal compared to control shown in FIG. 22E. Inserts in FIG. 22D and FIG. 22E showed overview of macular structure, with scale bar=50 μm.

Figure 23:
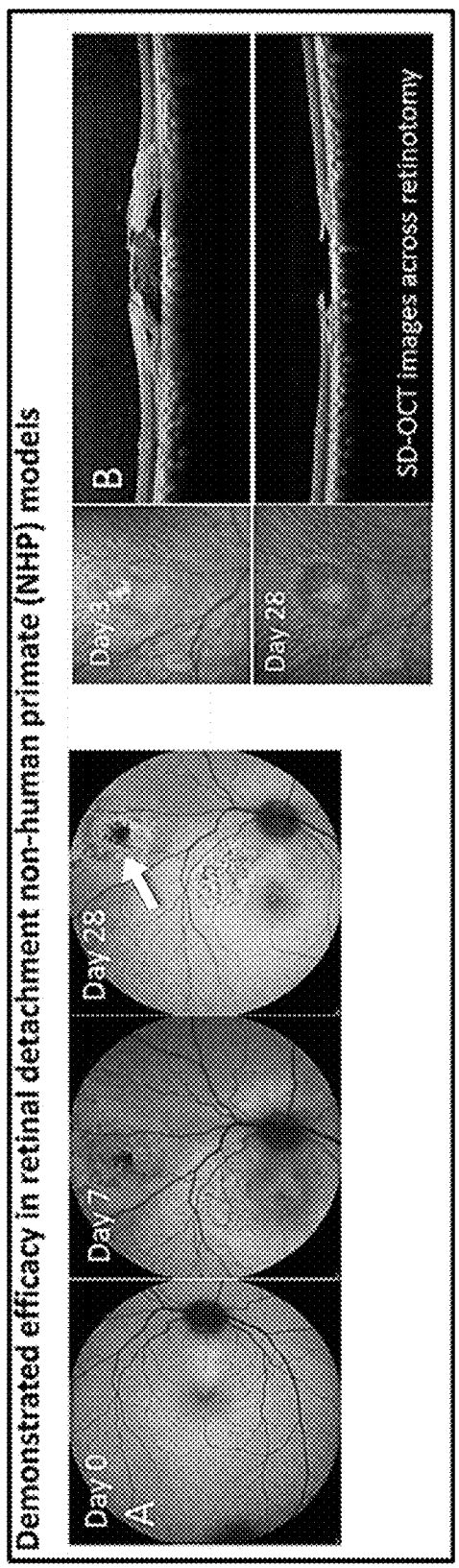
FIG. 23 shows auto-fluorescence images and SD-OCT images of retina post-retina detachment surgery (white arrow indicates sealed retinotomy site).

FIG. 23A shows that retina is flat at 1-month post-surgery with hydrogel intact. The SD-OCT images in FIG. 23B confirmed a re-attached retina.

At 3-months post-operation, the vitreous cavity remained optically clear. There was no evidence of anterior segment inflammation or cataract formation. Importantly, the IOP remained within a normal range of 12-17 mmHg (FIG. 21B). Furthermore, the retina remained attached at 12 months, and this was achieved without strict prone positioning, which cannot be enforced in NHPs. This demonstrates the ability of the presently disclosed gel to function as an effective internal tamponade through surface tension and swelling counter force, without a need to rely on buoyancy as with gas or oil.

Live in vivo OCT imaging of the macula at both 3 and 12 months revealed normal retinal architecture, with healed retinotomy sites. At 1-month post-surgery, on ERG, although there was mild cone and rod dysfunction on full-field ERG, there was a dramatic recovery by 3 months, and a full recovery by 12 months. Pattern ERG showed normal waveform at 12 months consistent with normal macular function. Histological analysis of Haemotoxylin and Eosin (H&E) stained tissue revealed a normal macular architecture in gel filled eyes compared to control.

Example 6: Demonstration of Biodegradability of EPC Thermogels

Figure 24:
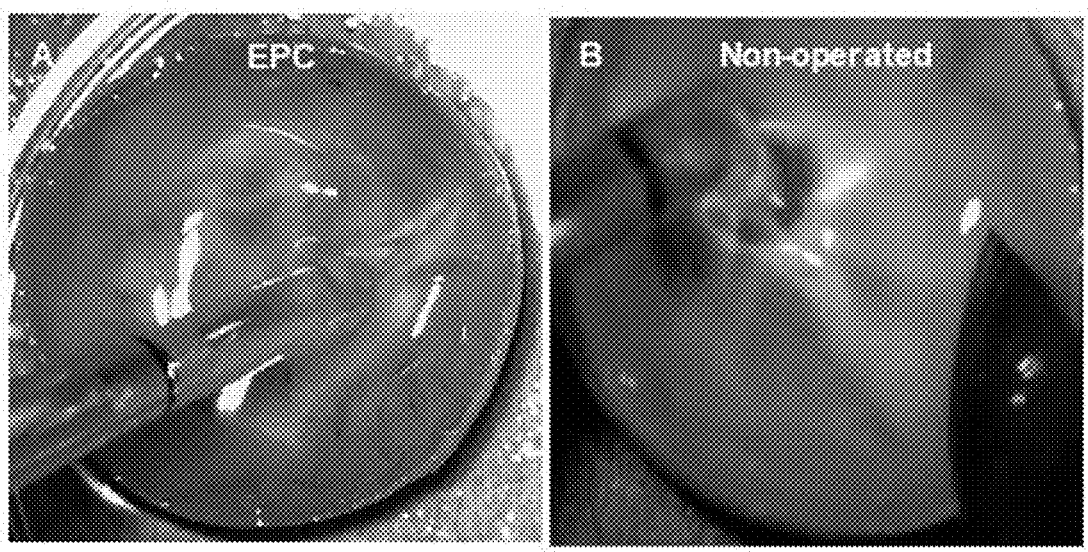
FIG. 24 shows proteome profile of EPC reformed vitreous-like body (A) Gross dissection of rabbit eye implanted with 7% EPC gel at 3-month post implantation: a vitreous like body of consistency similar to native vitreous (B) was observed.
Figure 25A:
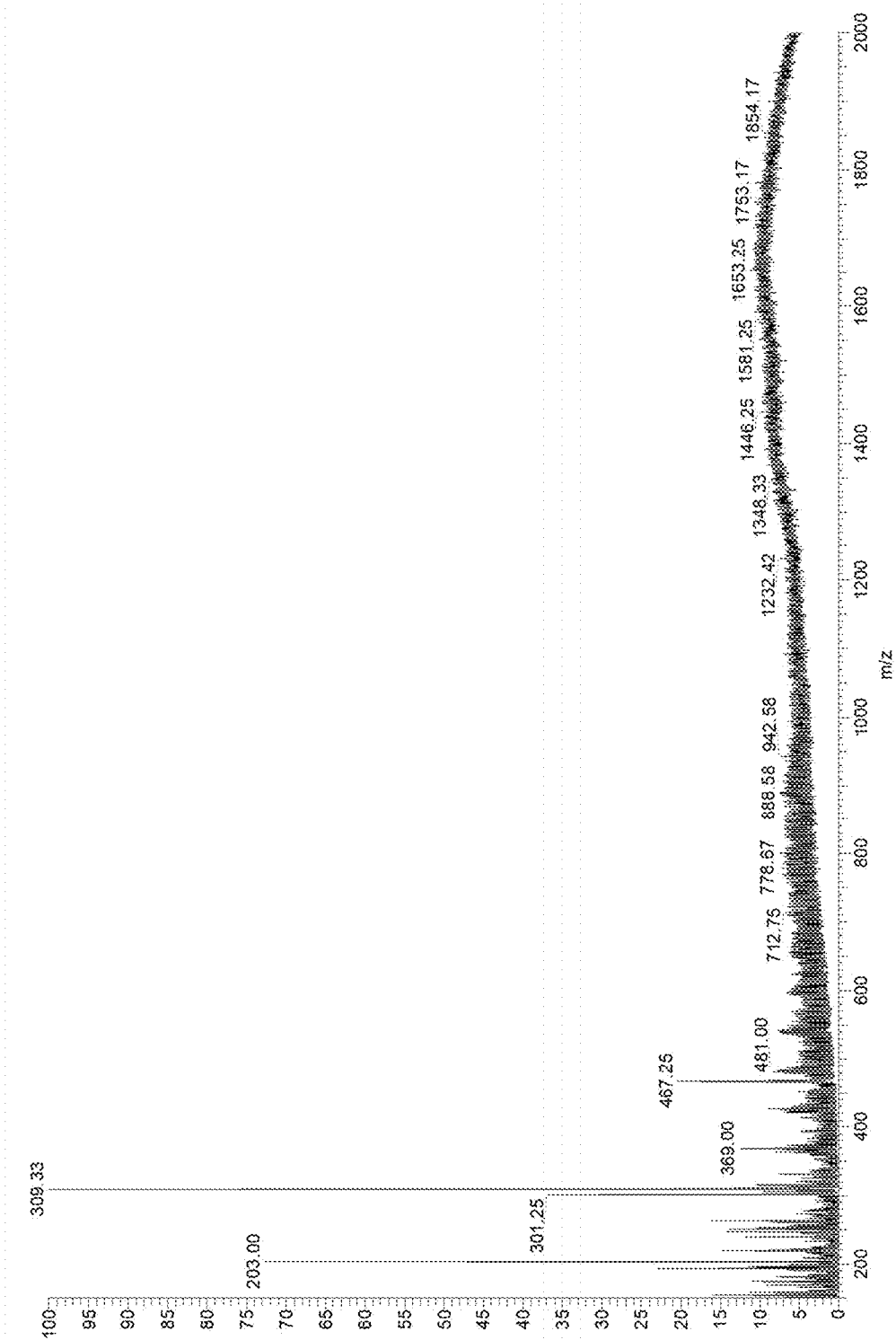
FIGS. 25A to 25D show mass-spectrometry (MS) analysis of EPC 7% thermogel at 3-months post-operation.
Figure 25B:
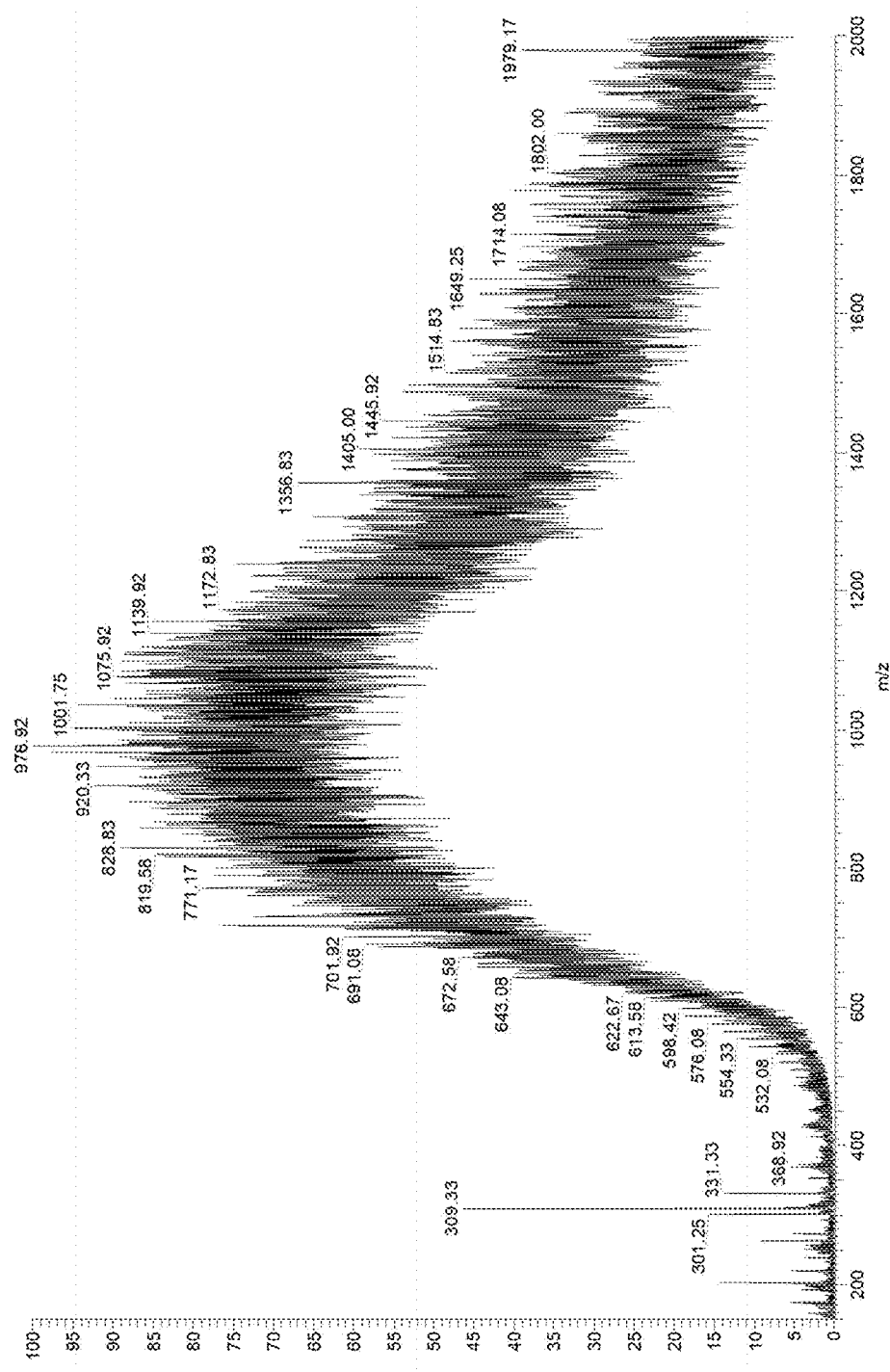
Figure 25C:
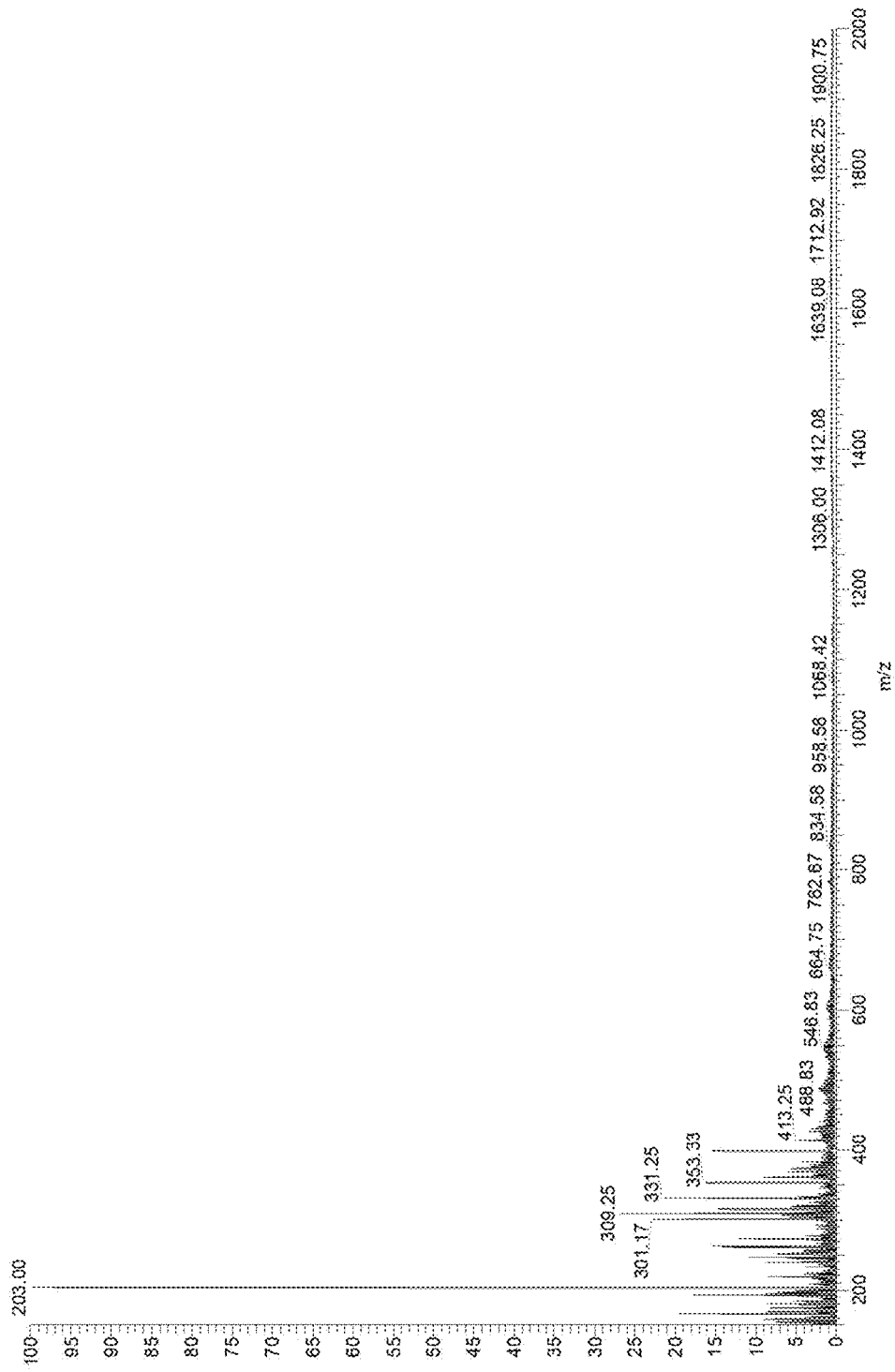
Figure 25D:
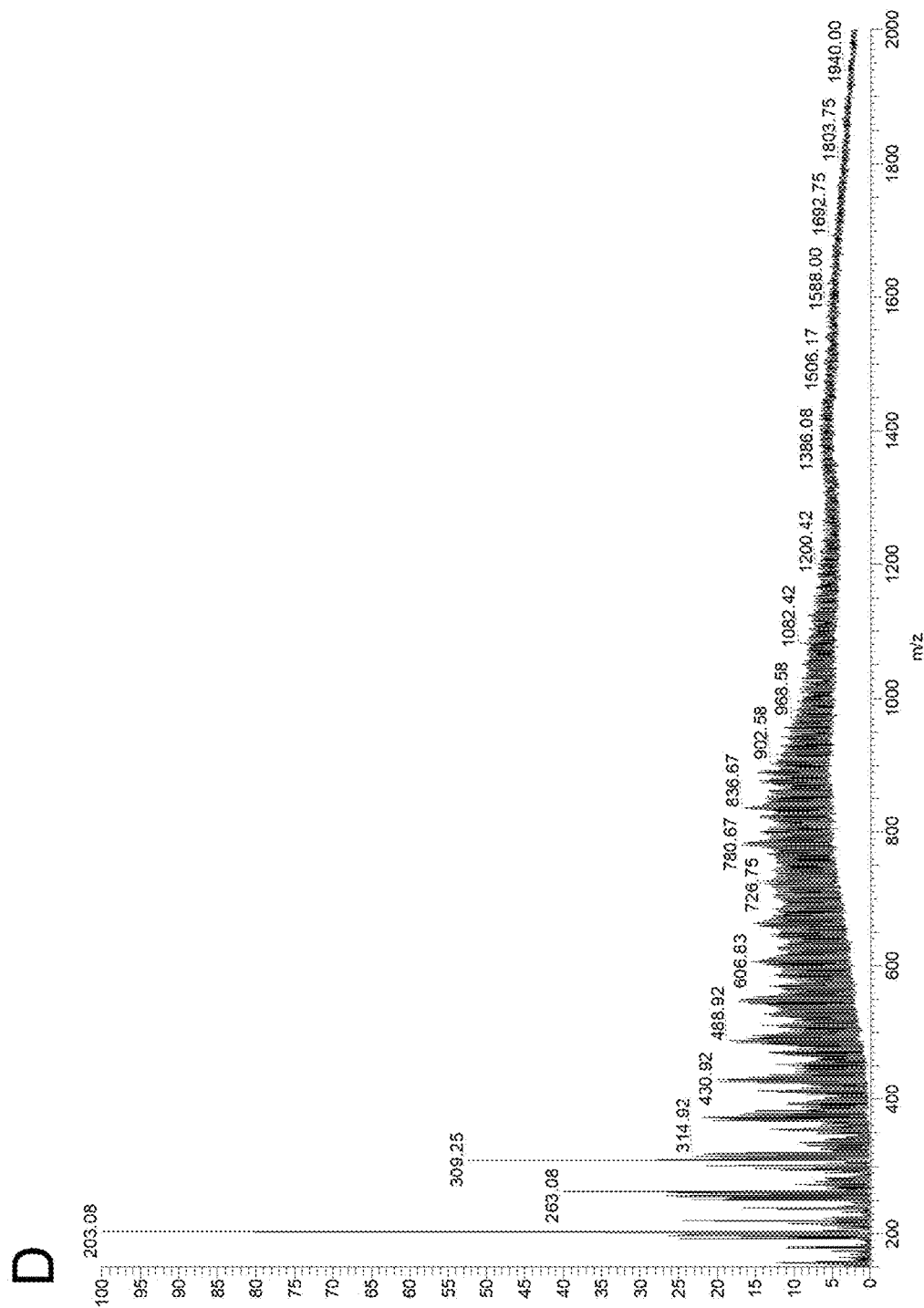
Figure 26A:
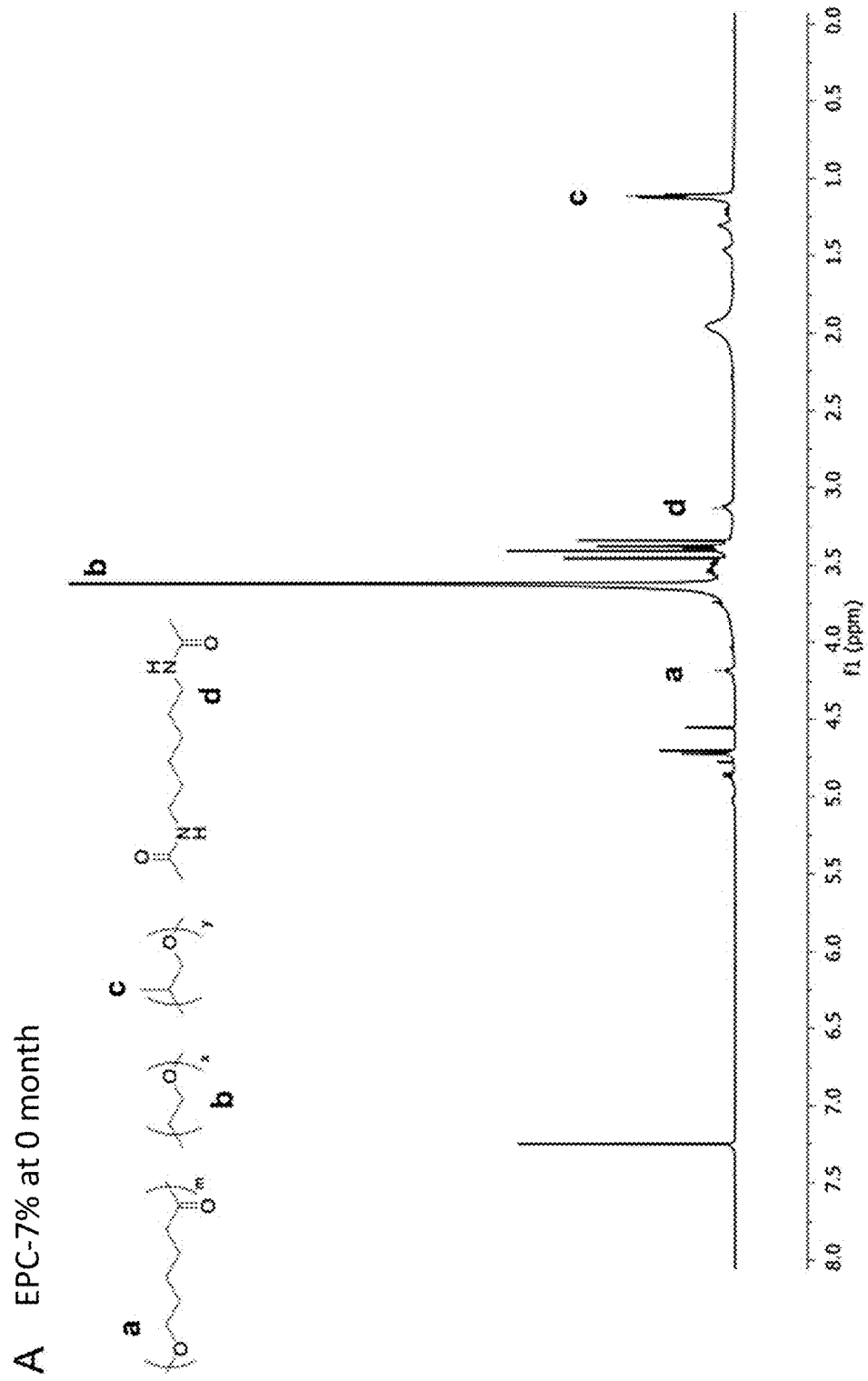
FIGS. 26A to 26C show $^1$H NMR spectra (in $CDCl_3$, 25° C.) of EPC-7% reformed vitreous-like body samples from rabbit eyes at 2 and 3-months post-operation.
Figure 26B:
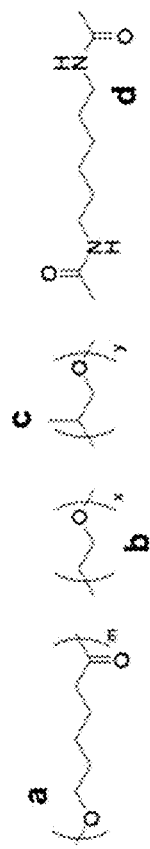
Figure 26B:
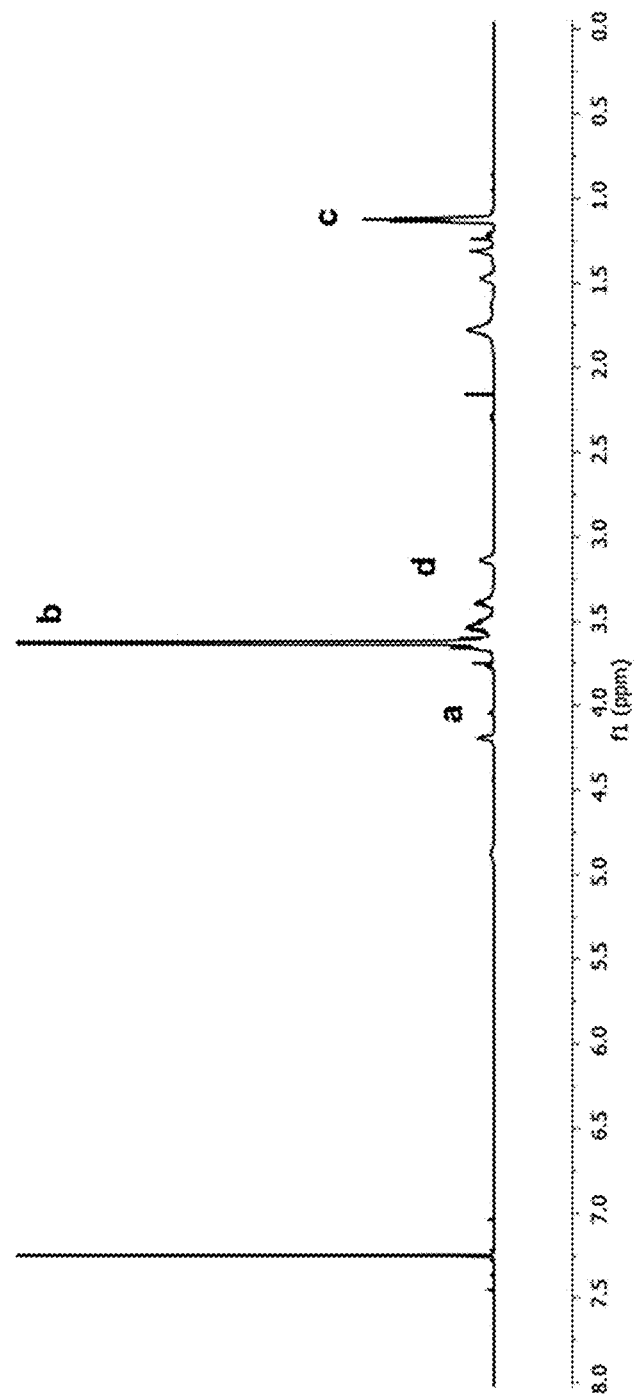
Figure 26C:
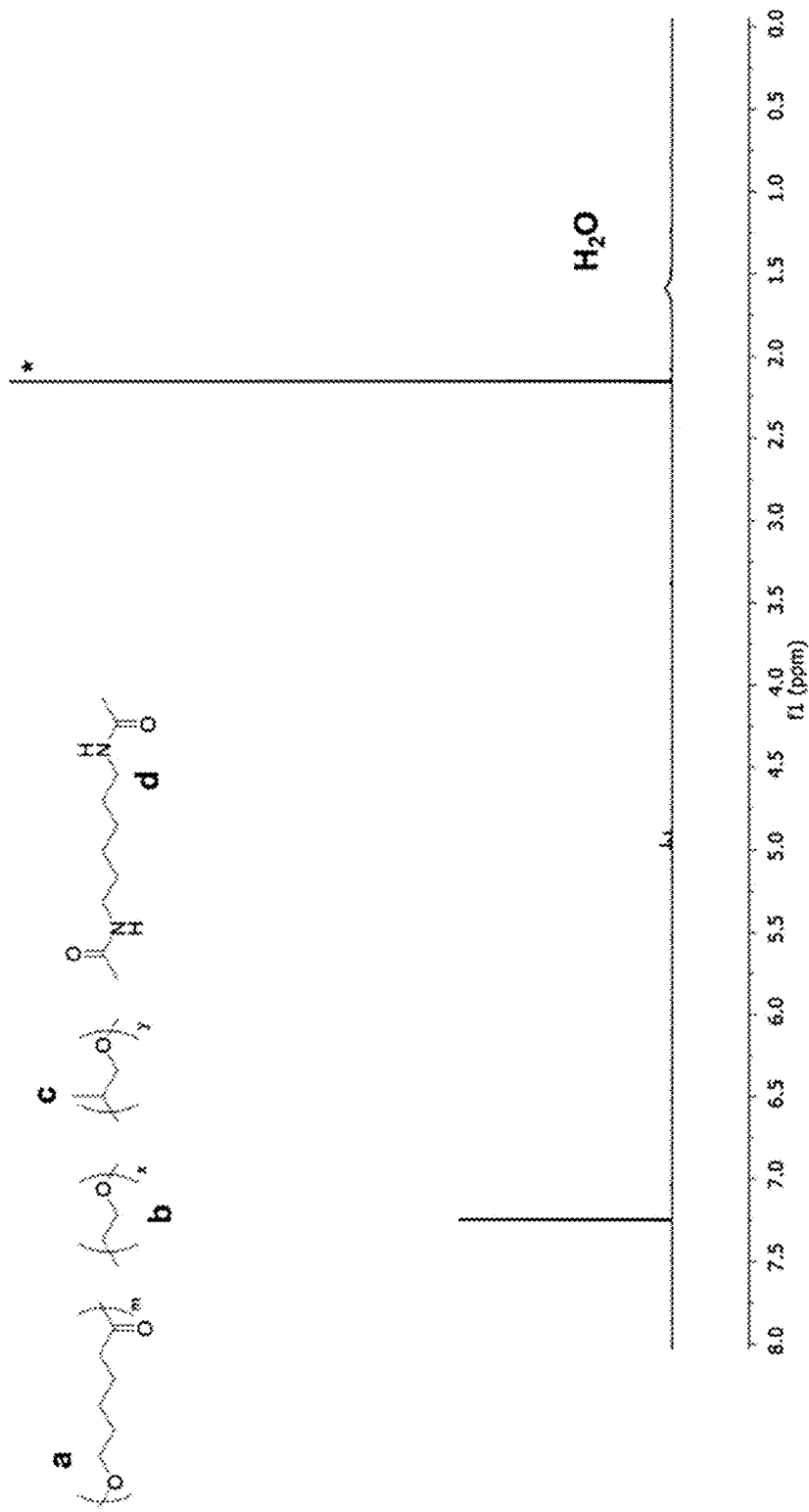

Upon dissection of the enucleated rabbit globes at 3-months post-surgery, a vitreous-like body formed, with a consistency reminiscent of native vitreous (FIG. 24). To show that the gel is no longer present by 3-months, consistent with its biodegradability property, the gel polymer is no longer detected by either mass-spectrometry (MS) analysis (FIGS. 25A to 25D) or nuclear magnetic resonance (NMR) (FIGS. 26A to 26C) at 3 months.

Mass spectrometry-based proteomics analysis was performed to characterize this vitreous-like material. Of 1177 proteins identified in native vitreous, 924 proteins were also identified in the gel induced vitreous-like body at 6-month post-implantation, indicating higher similarity between them.

Figure 27:
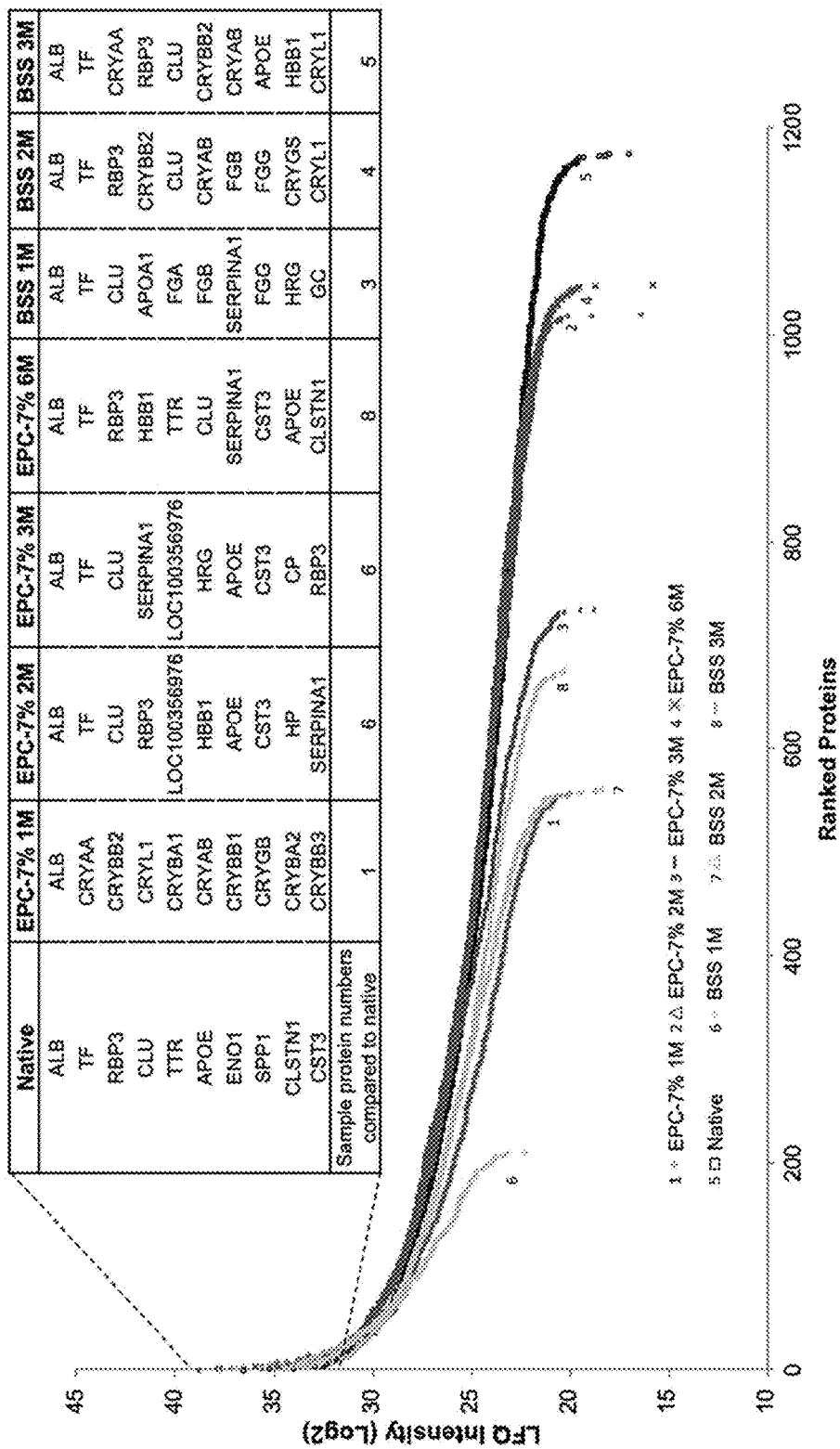
FIG. 27 shows a comparison of ranked protein abundances from highest to lowest based on label-free quantification (LFQ) intensities across the native, EPC reformed and BSS control proteome. The inset represents the top 10 proteins in each group according to protein intensities.

Comparison of ranked protein abundances from highest to lowest based on label-free quantification (LFQ) intensities across the native, EPC reformed and BSS control proteome is provided in FIG. 27. Only proteins reliably quantified across three replicates were visualized. The inset represents the top 10 proteins in each group according to protein intensities.

Figure 28:
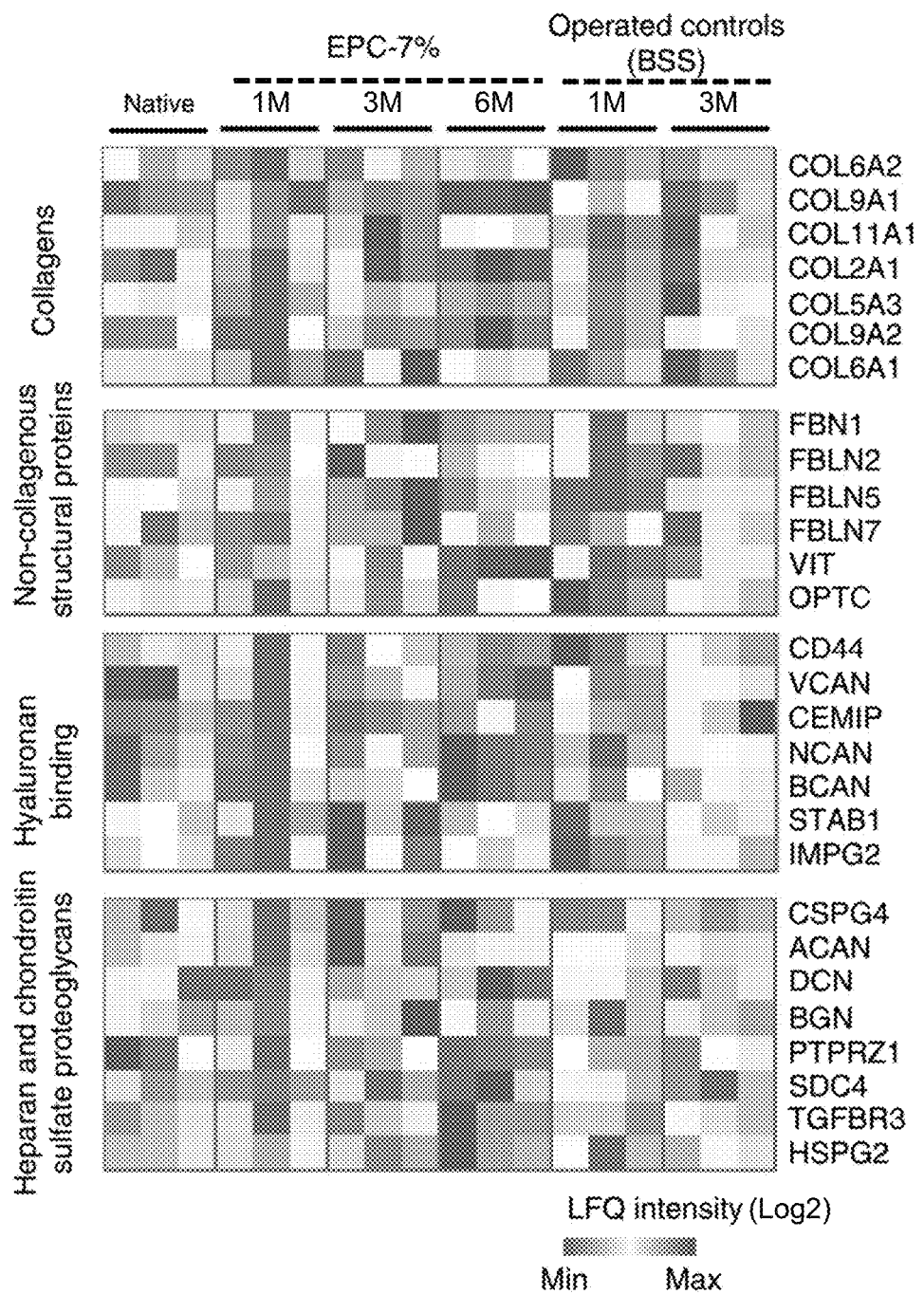
FIG. 28 is a heat map showing the expression of known vitreous structural components in EPC reformed vitreous-like body, compared to native vitreous and operated controls.

A heat map showing the expression of known vitreous structural components in EPC reformed vitreous-like body, compared to native vitreous and operated controls is provided in FIG. 28.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

The invention claimed is:

1. A material comprising a multi-block thermogelling polymer, said multi-block thermogelling polymer consisting of one or more of a first poly(alkylene glycol) block; one or more of a second poly(alkylene glycol) block; and one or more of a polyester block,
   wherein the first poly(alkylene glycol) block, the second poly(alkylene glycol) block and the polyester block are chemically coupled together by at least a urethane/carbamate linkage,
   wherein the first poly(alkylene glycol) block is different from the second poly(alkylene glycol) block,
   and wherein the material is suitable for use as a vitreous substitute.

2. The material of claim 1, wherein the first poly(alkylene glycol) block is poly(ethylene glycol) (PEG) and the second poly(alkylene glycol) block is poly(propylene glycol) (PPG).

3. The material of claim 1, wherein the polyester block is poly(caprolactone) (PCL).

4. The material of claim 1, wherein the molar ratio of the first poly(alkylene glycol) block to the second poly(alkylene glycol) block is in the range of 1:1 to 10:1.

5. The material of claim 1, wherein the polyester block is in an amount of from 1 wt % to 10 wt % of the multi-block thermogelling polymer.

6. The material of claim 1, wherein the material comprises 1% to 30% w/v of the multi-block thermogelling polymer in an aqueous medium.

7. The material of claim 1, wherein the material has a high water content of more than 60% by weight.

8. The material of claim 1, wherein the material has a pH value in a range of from 7.1 to 7.7.

9. The material of claim 1, wherein the material is in a flowable state at a temperature falling in the range of 20° C. to 30° C. and is in a non-flowable gel-like state at a temperature falling in the range of 36° C. to 40° C.

10. The material of claim 1, wherein the material is substantially transparent and/or has a refractive index falling in the range of from 1.20 to 1.48.

11. The material of claim 1, wherein the material is substantially devoid of a metal.

12. A method of preparing a material of claim 1, the method comprising:
   coupling one or more hydrophilic polymer, one or more thermosensitive polymer and one or more hydrophobic polymer together such that the hydrophilic polymer block, the thermosensitive polymer block and the hydrophobic polymer block are chemically coupled together by at least one of urethane/carbamate, carbonate, ester linkages or combinations thereof to form a multi-block polymer.

13. The method according to claim 12, wherein the one or more hydrophilic blocks, one or more thermosensitive blocks and one or more hydrophobic blocks are mixed in a molar ratio of 1-10: 1: 0.01-1.5,
   optionally wherein the mixing step is performed at an elevated temperature in the range of from 70° C. to 150° C., and
   optionally wherein the mixing step is carried out for at least 12 hours.

14. The method according to claim 12, wherein the coupling step is carried out in the presence of a coupling agent and the coupling agent comprises an isocyanate monomer that contains at least two isocyanate functional groups, optionally wherein the coupling agent is a diisocyanate selected from the group consisting of hexamethylene diisocyanate, tetramethylene diisocyanate, cyclohexane diisocyanate, tetramethylxylene diisocyanate, dodecylene diisocyanate, tolylene 2,4-diisocyanate and tolylene 2,6-diisocyanate.

15. The method according to claim 12, wherein the coupling step is carried out in the presence of an anhydrous solvent selected from the group consisting of toluene, benzene and xylene and/or wherein the coupling step is carried out in the presence of a tin catalyst selected from the group consisting of alkyltin compounds, aryltin compounds and dialkyltin diesters.

16. The method according to claim 12, the method further comprises
    removing the multi-block polymer of contaminants; and
    solubilizing the multi-block polymer in aqueous medium to form a multi-block thermogelling polymer.

17. A synthetic vitreous humour or part thereof comprising the material of claim 1.

18. The material of claim 1, wherein the first poly(alkylene glycol) block, the second poly(alkylene glycol) block and the polyester block are each linked to a respective adjacent block by a urethane/carbamate linkage.

19. The material of claim 2, wherein the molar ratio of PEG to PPG is in a range of 2:1 to 6:1.

20. The material of claim 19, wherein the molar ratio of PEG to PPG is 4:1.

21. The material of claim 3, wherein the PCL is derived from PCL-diol.

22. The material of claim 1,
    wherein the first poly(alkylene glycol) block is poly(ethylene glycol) (PEG),
    wherein the second poly(alkylene glycol) block is poly(propylene glycol) (PPG),
    wherein the polyester block is poly(caprolactone) (PCL),
    wherein the molar ratio of PEG to PPG is in a range of 2:1 to 6:1, and wherein the PCL is derived from PCL-diol.

* * * * *